(12) United States Patent
Wang et al.

(10) Patent No.: US 9,678,032 B2
(45) Date of Patent: Jun. 13, 2017

(54) CHEMOMETRIC ANALYSIS OF CHEMICAL AGENTS USING ELECTROCHEMICAL DETECTION AND CLASSIFICATION TECHNIQUES

(71) Applicants: The Regents of the University of California, Oakland, CA (US); Universitat Autonoma de Barcelona, Bellaterra (ES)

(72) Inventors: Joseph Wang, San Diego, CA (US); Joshua Ray Windmiller, Del Mar, CA (US); Aoife O'Mahony, San Diego, CA (US); Xavier Cetó, La Figuerosa (ES); Manel Del Valle, Terrassa (ES)

(73) Assignees: The Regents Of The University Of California, Oakland, CA (US); Universitat Autonoma De Barcelona, Bellatera (Barcelona) (ES)

( * ) Notice: Subject to any disclaimer, the term of this patent is extended or adjusted under 35 U.S.C. 154(b) by 0 days.

(21) Appl. No.: 14/439,641

(22) PCT Filed: Oct. 29, 2013

(86) PCT No.: PCT/US2013/067355
§ 371 (c)(1),
(2) Date: Apr. 29, 2015

(87) PCT Pub. No.: WO2014/070801
PCT Pub. Date: May 8, 2014

(65) Prior Publication Data
US 2015/0293048 A1  Oct. 15, 2015

Related U.S. Application Data

(60) Provisional application No. 61/719,911, filed on Oct. 29, 2012.

(51) Int. Cl.
*G01N 27/327* (2006.01)
*G01N 27/30* (2006.01)
(Continued)

(52) U.S. Cl.
CPC ....... *G01N 27/307* (2013.01); *G01N 33/0057* (2013.01); *G01N 27/48* (2013.01)

(58) Field of Classification Search
CPC ... G01N 27/307; G01N 27/48; G01N 33/0057
See application file for complete search history.

(56) References Cited

U.S. PATENT DOCUMENTS 6,290,838 B1    9/2001   Mifsud et al.
6,613,576 B1    9/2003   Rodacy et al.
(Continued)

FOREIGN PATENT DOCUMENTS

| WO | WO 2010/111484 | * | 9/2010 |
| WO | 2011103161 A2 | | 8/2011 |
| WO | WO 2011/156095 | * | 12/2011 |

OTHER PUBLICATIONS

Aoife, M. et al . . . "Swipe and Sccan: Integration of sampling and analysis of gunshot metal residues at screen-swiped electrodes," Electrochemistry Communications, 13:52-53, Jul. 2012.
(Continued)

*Primary Examiner* — Luan Van
*Assistant Examiner* — Steven E Rosenwald
(74) *Attorney, Agent, or Firm* — Perkins Coie LLP

(57) ABSTRACT

Methods, systems, and devices are disclosed for the identification of chemical agents and determination of their level of exposure using electrochemical detection and advanced signal processing. In one aspect, a method includes collecting a sample from a surface containing a chemical agent to an electrode on a sensor such that the chemical agent transfers on the electrode, detecting an electrochemical
(Continued)

signal of the chemical agent on the electrode to transduce chemical information associated with the chemical agent to an electrical signal, processing the electrical signal to obtain electrochemical spectral signature data to identify the chemical agent and generating a series of coefficients of the electrochemical spectral signature data to reduce the data, and classifying the chemical information based on the series of coefficients among preselected data sets to determine a level of exposure to the chemical agent.

15 Claims, 14 Drawing Sheets

(51) Int. Cl.
  *G01N 33/00* (2006.01)
  *G01N 27/48* (2006.01)

(56) References Cited

U.S. PATENT DOCUMENTS

| | | |
|---|---|---|
| 6,975,944 B1 | 12/2005 | Zenhausern |
| 7,410,612 B1 | 8/2008 | Carrington |
| 2006/0193750 A1* | 8/2006 | Filanovsky ........ G01N 27/4045 422/94 |
| 2007/0045243 A1 | 3/2007 | Sinha |
| 2010/0000882 A1* | 1/2010 | Wang ..................... G01N 33/22 205/781 |

OTHER PUBLICATIONS

J. Buena et al. "Raman Spectroscopic Analysis of Gunshot Residue Offering GreatPotential for Caliber Differentiation," Analytical Chemistry, 2012, pp. 4334-4339.

M. O. Salles et al. "Use of a Gold Microelectrode for Discrimination of Gunshot Residues," Sensors and Actuators B: Chemical, 2012, pp. 848-852.

Ceto et al. "Rapid field identification of subjects involved in firearm-related crimes based on electroanalysis coupled with advanced chemornetric data treatment," Analytical Chemistry, 2012, pp. 1 0306-10314.

Vuki et al., "Simultaneous electrochemical measurement of metal and organic propellant constituents of gunshot residues", Analyst, Apr. 2012, pp. 3265-3270.

* cited by examiner

CHEMOMETRIC ANALYSIS OF CHEMICAL AGENTS USING ELECTROCHEMICAL DETECTION AND CLASSIFICATION TECHNIQUES

CROSS REFERENCE TO RELATED APPLICATIONS

This patent document is a 35 USC §371 National Stage application of International Application No. PCT/US2013/067355 filed Oct. 29, 2013, which further claims the benefit of priority of U.S. Provisional Patent Application No. 61/719,911, entitled "CHEMOMETRIC IDENTIFICATION OF CHEMICAL AGENTS USING ELECTROCHEMICAL DETECTION AND CLASSIFICATION ALGORITHMS," filed on Oct. 29, 2012. The entire content of the above patent applications are incorporated by reference as part of the disclosure of this patent document.

STATEMENT REGARDING FEDERALLY SPONSORED RESEARCH OR DEVELOPMENT

This invention was made with government support under grant HQ0034-11-C-0034 awarded by the United States Army. The government has certain rights in the invention.

TECHNICAL FIELD

This patent document relates to systems, devices, and processes for electrochemical sensing and detection and extraction of chemical information.

BACKGROUND

Sensors based on electrochemical processes can be used to detect a chemical, substance, a biological substance (e.g., an organism) by using a transducing element to convert a detection event into a signal for processing and/or display. Biosensors can use biological materials as the biologically sensitive component, e.g., such as biomolecules including enzymes, antibodies, nucleic acids, etc., as well as living cells. For example, molecular biosensors can be configured to use specific chemical properties or molecular recognition mechanisms to identify target agents. Biosensors can use the transducer element to transform a signal resulting from the detection of an analyte by the biologically sensitive component into a different signal that can be addressed by optical, electronic or other means. For example, the transduction mechanisms can include physicochemical, electrochemical, optical, piezoelectric, as well as other transduction means.

SUMMARY

Techniques, systems, and devices are disclosed for identification of chemical agents using a electrochemical detection and advanced signal processing algorithms to transduce chemical information to the electrical domain, e.g., which can be performed at a single electrode contingent.

In one aspect, a method to identify and analyze exposure levels of a chemical agent includes collecting a sample from a surface containing a chemical agent to an electrode on a sensor to cause contact between the chemical agent and the electrode, detecting an electrochemical signal of the chemical agent on the electrode to transduce chemical information associated with the chemical agent to an electrical signal, processing the electrical signal to generate data to obtain an electrochemical spectral signature from the data to identify the chemical agent, generating a series of coefficients of the electrochemical spectral signature to compress the data, and classifying the chemical information based on the series of coefficients among preselected data sets to determine a level of exposure to the chemical agent.

Implementations of the method can optionally include one or more of the following features. For example, in some implementations of the method, the collecting can include swiping the surface using the electrode surface of the sensor. For example, the sensor can include a printed three-electrode strip including a working electrode, a counter electrode, and a reference electrode, in which the chemical agent is transferred to the working electrode. For example, the sensor can include a printed two-electrode strip including a working electrode and a reference electrode, in which the chemical agent is transferred to the working electrode. In some implementations of the method, for example, the detecting the electrochemical signal can include performing at least one of voltammetry, cyclic voltammetry, square wave voltammetry, differential pulse voltammetry, amperometry, chronoamperometry, potentiometry, chronopotentiometry, coulometry, chronocoulometry, conductometry, and/or impedometry. In some implementations of the method, for example, the generating the series of coefficients of the electrochemical spectral signature can include using a discrete Wavelet transform (DWT) or a fast Fourier transform (FFT). For example, the method can include using the DWT or the FFT to filter noise from the electrical signal. In some implementations of the method, for example, the classifying can include performing pattern recognition using the preselected data sets and the series of coefficients to assign a group membership or ranking to the chemical information by maximizing inter-group variance between unique groups and minimizing intra-group variance. For example, the pattern recognition can include at least one of principal component analysis (PCA), analysis of variance (ANOVA), regression analysis, Fisher's linear discriminant (FLD), linear discriminant analysis (LDA), quadratic discriminant analysis (QDA), neural networks, perceptrons, support vector machines, Bayes classifiers, kernel estimation, decision trees, maximum entropy classifier, or K-means clustering.

In some implementations of the method, for example, the chemical agent can include gunshot residue (GSR) and/or explosive residue (ER). For example, the level of exposure to the GSR can be classified into a plurality of groups including a No Contact group, a Secondary Contact group, and a Primary Contact group. For example, the Secondary Contact group can include subjects that have been present in an environment where a firearm was discharged (a) without a subject handling the firearm or (b) with the subject handling the firearm but not firing it. For example, the Primary Contact group can include subjects that have fired a firearm. For example, the Primary Contact group can also include subjects that have fired the firearm and washed their hands subsequent to the firing of the firearm.

In another aspect, a chemical analysis system includes an electrode strip to collect a sample from a surface containing a chemical agent, an electrochemical analysis unit structured to receive the electrode strip to transduce chemical information associated with the chemical agent to an electrical signal, and a data processing unit in communication with the electrochemical analysis unit and structured to include one or more memory units and one or more processors configured to process the electrical signals as data to identify the chemical agent by determining an electrochemical spectral signature based on the chemical information contained in the transduced electrical signal. The electrode strip of the chemical analysis system includes a substrate of an electrically insulative material, a plurality of electrodes on the substrate forming a single electrode contingent for an electrochemical analysis, and electrode interface contacts on the substrate and electrically coupled to the electrodes via electrically conductive conduits.

Implementations of the system can optionally include one or more of the following features. For example, in some implementations of the system, the data processing unit can be configured to determine a level of exposure of the sample to the chemical agent by generating a series of coefficients of the electrochemical spectral signature to compress the data, and classifying the chemical information based on the series of coefficients among preselected data sets to determine a level of exposure to the chemical agent, in which the classifying includes performing pattern recognition using the preselected data sets and the series of coefficients to assign a group membership or ranking to the chemical information by maximizing inter-group variance between unique groups and minimizing intra-group variance. In some implementations of the system, for example, data processing unit can generate the series of coefficients of the electrochemical spectral signature using a DWT or a FFT. For example, the data processing unit can use the DWT or the FFT to filter noise from the electrical signal. For example, the data processing unit can classify the chemical information by using at least one of PCA, ANOVA, regression analysis, FLD, LDA, QDA, neural networks, perceptrons, support vector machines, Bayes classifiers, kernel estimation, decision trees, maximum entropy classifier, and/or K-means clustering. In some implementations, for example, the single electrode contingent of the electrode strip can include (i) one working electrode and one reference electrode or (ii) one working electrode, one counter electrode, and one reference electrode. For example, the electrode strip can further include an electrically insulative layer formed over a region of the substrate between the electrodes and the electrode interface contacts. In some implementations of the system, for example, the electrochemical analysis unit can be configured in a portable device and the data processing unit can be configured in a remote computer, in which the portable device includes a processor and memory unit coupled to the electrochemical analysis unit, and a transmitter unit to transmit the transduced electrical signal as transmitted data to the remote computer, in which the remote computer is in communication with the portable device via a communication network or link to receive the transmitted data and process the transmitted data to identify the chemical agent and determine the level of exposure of the sample to the chemical agent.

In some implementations of the system, for example, the chemical agent can include GSR and/or ER. For example, the data processing unit can classify the level of exposure to the GSR into a plurality of groups including a No Contact group, a Secondary Contact group, and a Primary Contact group. In some implementations of the system, for example, the electrochemical analysis unit and data processing unit can be configured in a portable device to identify the chemical agent and determine the level of exposure of the sample to the chemical agent. In such exemplary implementations, for example, the system further includes a remote computer in communication with the portable device via a communication network or link to receive the processed data including the classified chemical information from the portable device and to process the classified chemical information in a data library of previously collected samples.

In another aspect, an integrated electrode device to collect and analyze a sample includes a substrate of an electrically insulative material, a plurality of electrodes of an electrically conductive material on the substrate forming a single electrode contingent for an electrochemical analysis of one or more chemical agents present in a sample collected on the integrated electrode device, in which the single electrode contingent of the electrode strip is structured to include (i) one working electrode and one reference electrode or (ii) one working electrode, one counter electrode, and one reference electrode, and electrode interface contacts on the substrate and electrically coupled to the electrodes via electrically conductive conduits, in which the integrated electrode device is operable for the electrochemical analysis when the sample is in physical contact with the working electrode and electrically coupled, via the electrode interface contacts, to an electrical circuit to transduce chemical information associated with the one or more chemical agents to an electrical signal.

Implementations of the device can optionally include one or more of the following features. For example, in some implementations, the device can further include an electrically insulative layer formed over a region of the substrate between the plurality of electrodes and the electrode interface contacts. In some implementations, for example, the integrated electrode device can be used to collect the sample by swiping a surface using the surface of the electrode contingent of the device.

In another aspect, a method to identify and analyze exposure levels of a chemical agent includes collecting a sample from a surface containing a chemical agent to an electrode on a sensor to cause a contact between the chemical agent and the electrode, detecting an electrochemical signal of the chemical agent on the electrode to transduce chemical information associated with the chemical agent to an electrical signal, processing the electrical signal to generate data to obtain an electrochemical spectral signature from the data to identify the chemical agent, and classifying the chemical information based on predetermined data indicating different levels of exposure to the chemical agent under different conditions to determine a level of exposure to the chemical agent from the sample.

Implementations of the method can optionally include one or more of the following features. For example, in some implementations, the method can further include compressing the data, prior to the classifying, to generate a series of coefficients of the electrochemical spectral signature. In such implementations, for example, the classifying can include performing pattern recognition using the predetermined data and the series of coefficients to assign a group membership or ranking to the chemical information by maximizing inter-group variance between unique groups and minimizing intra-group variance. For example, the pattern recognition can include at least one of PCA, ANOVA, regression analysis, FLD, LDA, QDA, neural networks, perceptrons, support vector machines, Bayes classifiers, kernel estimation, decision trees, maximum entropy classifier, or K-means clustering. In such implementations, for example, the compressing the data to generate the series of coefficients can include using a DWT or a FFT. For example, the method can further include using the DWT or the FFT to filter noise from the electrical signal.

In some implementations of the method, for example, the collecting can include swiping the surface using the electrode surface of the sensor. For example, the sensor can include a printed three-electrode strip or a printed two-electrode strip, wherein the three-electrode strip is structured to include a working electrode, a counter electrode, and a reference electrode, and the two-electrode strip is structured to include a working electrode and a reference electrode. For example, the detecting the electrochemical signal can include performing at least one of voltammetry, cyclic voltammetry, square wave voltammetry, differential pulse voltammetry, amperometry, chronoamperometry, potentiometry, chronopotentiometry, coulometry, chronocoulometry, conductometry, or impedometry. For example, in some implementations of the method, the chemical agent can include GSR or ER. For example, for determining the level of exposure to GSR, the predetermined data can include a plurality of groups of differing levels of exposure to GSR including a No Contact group, a Secondary Contact group, and a Primary Contact group. For example, the Secondary Contact group can include subjects that have been present in an environment where a firearm was discharged (a) without a subject handling the firearm or (b) with the subject handling the firearm but not firing it. For example, the Primary Contact group can include subjects that have fired a firearm, as well as subjects that have fired the firearm and washed their hands subsequent to the firing of the firearm.

The subject matter described in this patent document can be implemented in specific ways that provide one or more of the following features. The disclosed technology can be implemented to non-invasively identify chemical residues and/or constituents present on or within a sample. For example, such chemical residues can include, but is not limited to, explosive agents, nerve agents, toxins, pathogens, contaminants, and biological materials. In some implementations, for example, the disclosed devices and systems can provide a complete chemical analysis lab as a handheld, field-deployable unit requiring a minimally-trained individual to operate. Some exemplary applications of the disclosed technology include the identification of gunshot residue (GSR) for forensic applications, in which the disclosed technology is widely positioned to enable rapid chemical analysis in the field. The described electrochemical sensing and processing techniques of the disclosed technology can be implemented on a hand-held device to allow portability and speed in such forensic applications. For example, this can serve to provide a simple response outlining a subject's complicity in a crime involving the discharge of a firearm, whereby categories including 'free-to-go', 'witness to a shooting' and 'involved in a shooting' can be ascertained from this methodology. And in addition to forensics, for example, the disclosed technology can be applied to a wide-range of domains including healthcare, environmental, agricultural, and cosmetics, among others.

DETAILED DESCRIPTION

Figure 1A:
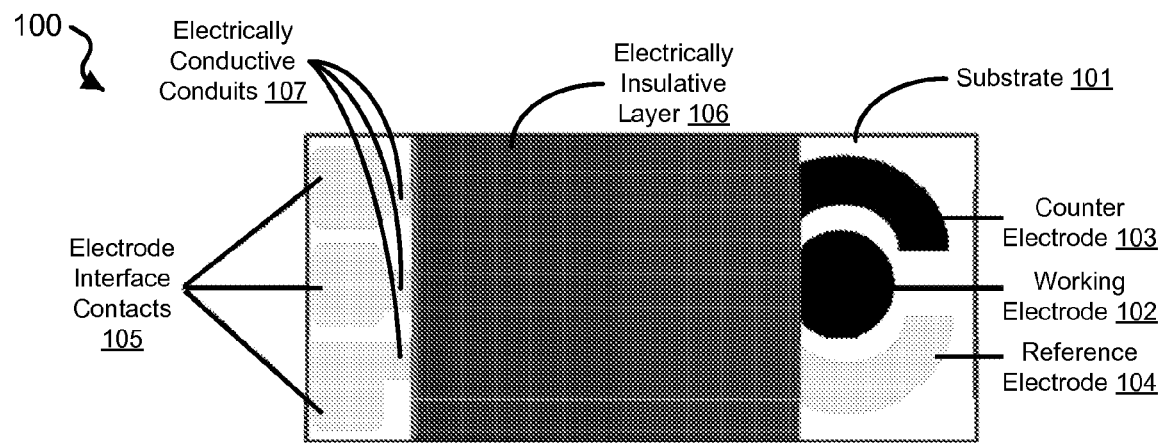
FIG. 1A shows a diagram of an exemplary electrochemical detection strip device of the disclosed technology.

Chemometrics is the science of extracting information from chemical systems by data processing analysis tools and techniques. In some examples, chemometrics can involve data analysis techniques from multivariate statistics, applied mathematics, and computer science disciplines for use in applications including chemistry, biochemistry, medicine, biology and chemical engineering, among others.

For example, some chemometric based methods and systems have been used to identify the constituents of food, cosmetics, and alcoholic beverages. These methods employ different mathematical transformations applied to the sample responses (e.g., either the raw recorded signal or the extracted coefficients after preprocessing) to build a model that allows more straightforward visualization of the similarities and differences between the different analyzed samples. These principles can be brought to a higher complexity level using an array of electrochemical sensors with a complementary response, using analysis systems referred to as an 'electronic tongue' or an 'electronic nose' analysis systems.

Disclosed are electrochemical detection techniques, devices, and systems and associated chemometric methods, systems, and devices for identification of chemical agents and determination of their level of exposure. For example, the disclosed technology includes electrochemical sensors having a single electrode contingent to detect the chemical agents.

In one aspect, a chemometric method of the disclosed technology to identify a chemical agent and determine a degree of exposure of the chemical agent includes collecting a sample from a surface that may contain one or more chemical agents of interest to an electrode contingent on a electrochemical sensor device, such that the chemical agent transfers on the electrode. The chemometric method includes performing an electrochemical detection, using the electrochemical sensor device, to transduce chemical information associated with the chemical agent on the electrode to an electrical signal. The chemometric method includes processing the electrical signal to obtain electrochemical spectral signature data, in which the processing includes reducing the obtained electrochemical spectral signatures to generate a series of coefficients that describe the electrochemical spectral waveform contained in the electrical signal. For example, by using the DWT and/or FFT techniques, excess noise can also be simultaneously filtered from the electrochemical spectral signature data. The chemometric method includes classifying the chemical information from the electrochemical spectral signature data among preselected data sets to identify the chemical agent by using a pattern recognition technique to generate a series of mathematical relations that maximize the variance between unique groups within the electrochemical spectral signature data and minimize in-group variance. For example, the preselected data sets can include a library of predetermined data indicating different levels of exposure to the chemical agent under different conditions. For example, the classifying using the pattern recognition technique can provide the discrimination between different sample clusters. In some examples of the pattern recognition techniques, the algorithm itself is a supervised method.

The disclosed chemometric method includes the amalgamation of electrochemical detection methods with pattern-recognition techniques. For example, electrochemical detection methods that can be implemented include voltammetry, amperometry, potentiometry, coulometry, conductometry, and/or impedometry. The pattern recognition techniques implemented by the disclosed technology can use Principal Component Analysis (PCA), Linear Discriminant Analysis (LDA), Support Vector Machines (SVMs), analysis of variance (ANOVA), regression analysis, Fisher's Linear Discriminant (FLD), Quadratic Discriminant Analysis (QDA), neural networks, perceptrons, Bayes classifiers, kernel estimation, decision trees, maximum entropy classifier, and/or K-means clustering.

The disclosed chemometric method involves three distinct components, e.g., including a sample collection routine, an electrochemical detection/transduction methodology, and signal processing of the data obtained from the electrochemical detection. In some applications, the method can be implemented for the classification of residues originating from the handling and discharge of a firearm or explosives and to implicate culpability under such scenarios. Additionally, the described techniques can be extended to a plethora of other diverse applications requiring differentiation among groups possessing variable chemical signatures.

In some implementations, for example, a sample is isolated by abrasive 'swiping' of the surface of interest using a single electrode contingent, e.g., such as a printed two- or three-electrode strip. For example, the printed two-electrode single electrode contingent includes a working electrode and a reference electrode; the printed three-electrode single electrode contingent includes a working electrode, counter electrode, and reference electrode. The printed electrode contingent can be fabricated using techniques including, but not limited to, screen printing, inkjet printing, aerosol deposition, roll-to-roll printing, or flexography on any one of a number of electrically insulative substrates, e.g., including, but not limited to, ceramics, plastic, rubber, fabrics, and textiles. In some implementations, for example, following abrasion of the surface, a buffer solution is dispensed on the electrode surface to wet the electrodes and serve as an electrolytic fluid. The electrode strip is subsequently inserted into an analyzer and any one of a number of electrochemical methods are performed, e.g., including voltammetry, amperometry, potentiometry, coulometry, conductometry, and/or impedometry in order to transduce the chemical information present on the electrode surface. These various electrochemical stimuli can yield a unique spectral signature/fingerprint corresponding to the presence of the analytes within the sample (or lack thereof). For example, in the case of gunshot residue (GSR) analysis, spectral signatures are generated due to the presence of metals (e.g., such as lead, antimony, and copper), organic propellants (e.g., such as nitrocellulose), inorganic oxidizers, and primer agents that are associated with the handling and/or discharge of a firearm/ammunition.

Figure 1B:
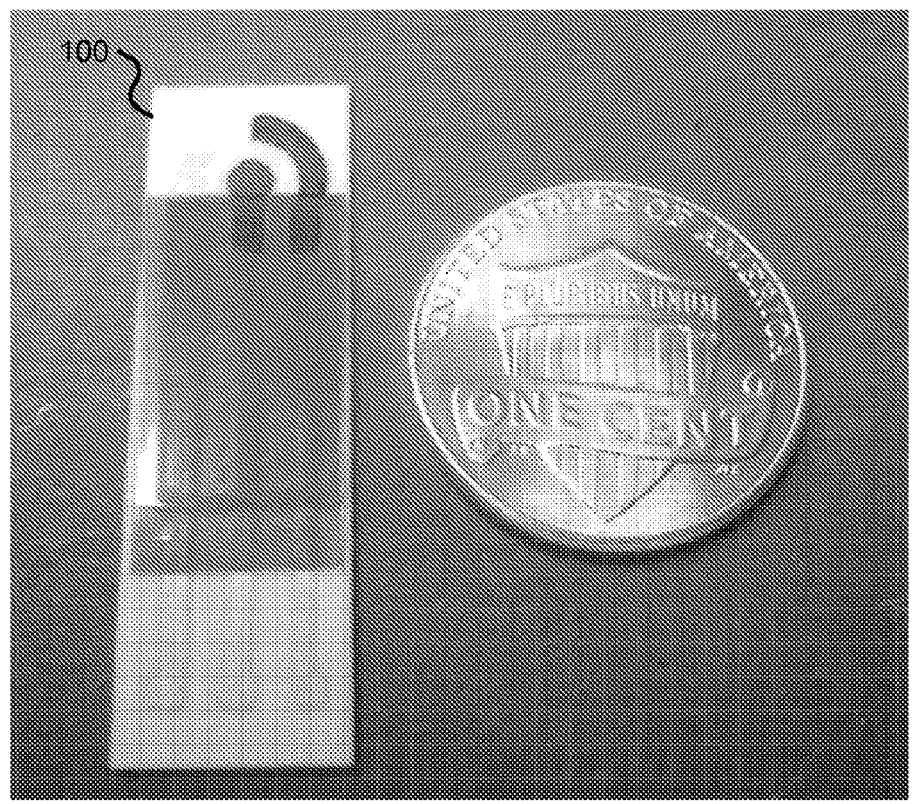
FIG. 1B shows an image of an exemplary three-electrode contingent strip.

FIG. 1A shows a diagram of an exemplary electrochemical sensor device 100 configured as an electrode strip that can be used to swipe a sample from a surface. The electrochemical sensor device 100 includes a substrate 101 formed of an electrically insulative material. The electrochemical sensor device 100 includes a plurality of electrodes on the substrate 101 and formed of at least one of an electrically conductive material or an electrically semi-conductive material. In some embodiments, for example, electrochemical sensor device 100 includes a three-electrode contingent including a working electrode 102, a counter electrode 103, and a reference electrode 104. In some embodiments, for example, electrochemical sensor device 100 includes a two-electrode contingent including the working electrode 102 and the reference electrode 104. The electrochemical sensor device 100 includes electrode interface contact components 105 formed on the substrate 101 and electrically coupled to the electrodes via electrically conductive conduits 107. As shown in FIG. 1A, the electrically conductive conduits 107 can be covered by an electrically insulative layer 106 formed over a region of the substrate between the electrodes and the electrode interface contacts 105. FIG. 1B shows an image of an exemplary electrode strip adjacent to a penny to demonstrate the relatively small size of the electrochemical sensor device 100.

The use of the working electrode in electrochemical analysis can provide high signal to noise and reproducible detection responses to chemical changes caused by the passage of an electric current. The exemplary two-electrode or three-electrode contingent of the device 100 can form an electrochemical analytical cell in the presence of an electrolyte, in which the working electrode 102 is the electrode at which the reaction of interest occurs, the reference electrode 104 provides a stable and reproducible potential (e.g., independent of the sample composition), against which the potential of the working electrode is compared. In voltammetry and amperometry forms of electrochemical analyses, the counter electrode 103 passes the current needed to balance the current observed at the working electrode 103.

The device 100 is operable to detect a substance on an external surface of the electrodes when the electrode interface contacts 105 are electrically coupled to one or more electrical circuits. For example, the device 100 is capable of acquiring the sample of the surface of the electrodes using the 'swipe' method of sampling to collect the target substance. For example, if the device 100 is used for voltammetry, the electrical circuit can include a voltammetric analyzer including potentiostatic circuitry and a voltage ramp generator. In operation, the electrical circuit can apply a time varying potential signal to the electrode contingent of the device 100 to record a spectroscopic profile (voltammogram) of chemical agents (analytes) present in the sample.

Following the transduction of the chemical information to an electrical signal via the electrochemical methods described above, the spectral envelope of the data is extracted to compress the signal while maintaining its shape and reducing the noise present in the measurement. For example, this can be implemented using a FFT or DWT. Following the exemplary data compression, the processing includes performing pattern-recognition to classify the data among pre-selected data sets. In one example, an LDA optimization algorithm is used to generate a series of mathematical relations that maximize the variance between unique groups while minimizing the in-group variance. This exemplary algorithm represents a supervised pattern recognition method, which enables the construction of and can use a library of previously collected samples under a wide array of scenarios and conditions.

Once the data is classified, for example, the user can be presented with an easy-to-assess readout delineating the pre-defined group (e.g., among a collection of groups/clusters) that the sample has been determined to occupy. Statistics based on confidence, accuracy, specificity, and sensitivity can be provided to the operator as quantifiable metrics. For example, in the case of GSR analysis, this unique ability can be used to discriminate between no exposure to GSR, secondary exposure from surfaces and air, exposure from loading a firearm, and primary exposure from the discharge of a firearm, e.g., providing a much-needed forensic tool to implicate suspects and identify culpability in the field.

Figure 1C:
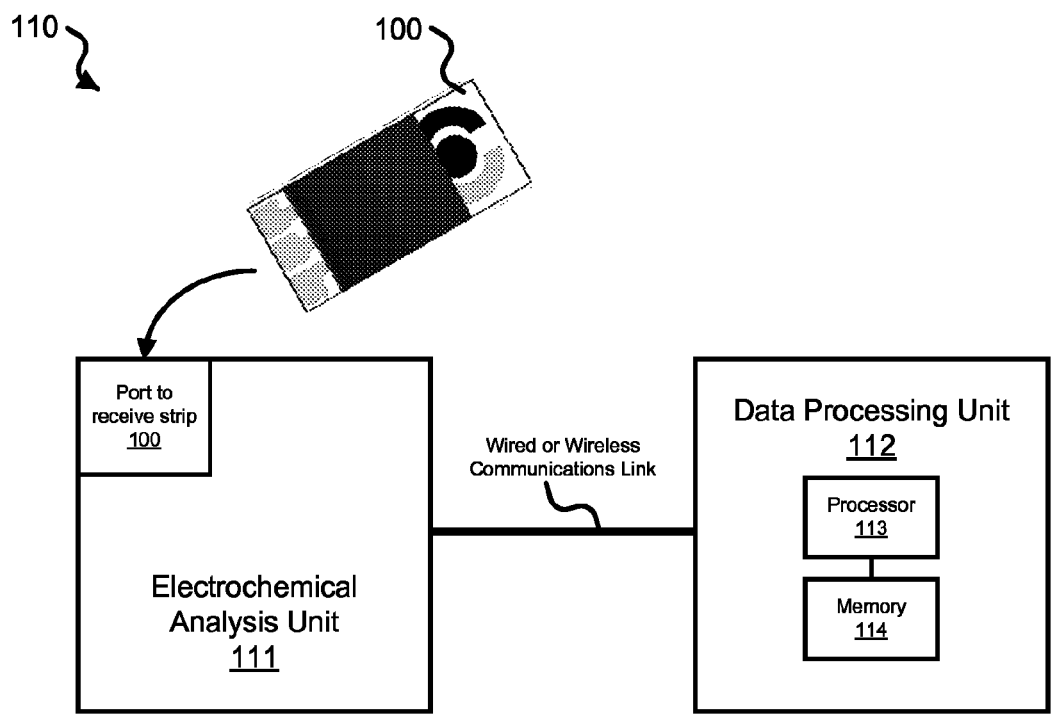
FIG. 1C shows a diagram of an exemplary chemical analysis system to identify a chemical agent of interest.

FIG. 1C shows a diagram of an exemplary chemical analysis system 110 to identify a chemical agent or agents present in a collected sample. In some implementations, for example, the system can also determine a level of exposure of the sample to the chemical agent. The chemical analysis system 110 includes the electrode strip 100 to collect a sample from a surface containing one or more chemical agents of interest by transferring the sample on the electrode contingent of the device 100. For example, the sample can be transferred by a swiping of the strip 100 on the surface containing the sample. The system 110 includes an electrochemical analysis unit 111 structured to receive the electrode strip 100 to transduce chemical information associated with the chemical agent to an electrical signal. The system 110 includes a data processing unit 112 in communication with the electrochemical analysis unit 111 and one or more processor units 113 communicatively coupled to one or more memory units 114 to process the electrical signals as data to identify the chemical agent by determining an electrochemical spectral signature based on the chemical information contained in the transduced electrical signal. For example, the electrochemical analysis unit 111 can be in communication with the data processing unit 112 via wired and/or wireless communication links. For example, the data processing unit 112 can include an input/output unit, e.g., which can include a transmitter and/or receiver, to control the input and output of data to the data processing unit 112. Some examples for wireless communications include 3G wireless communication standards, 4G wireless communication standards including, LTE, WiFi, Bluetooth, and other suitable wireless communications via radio frequency waves and other electromagnetic waves.

Figure 1D:
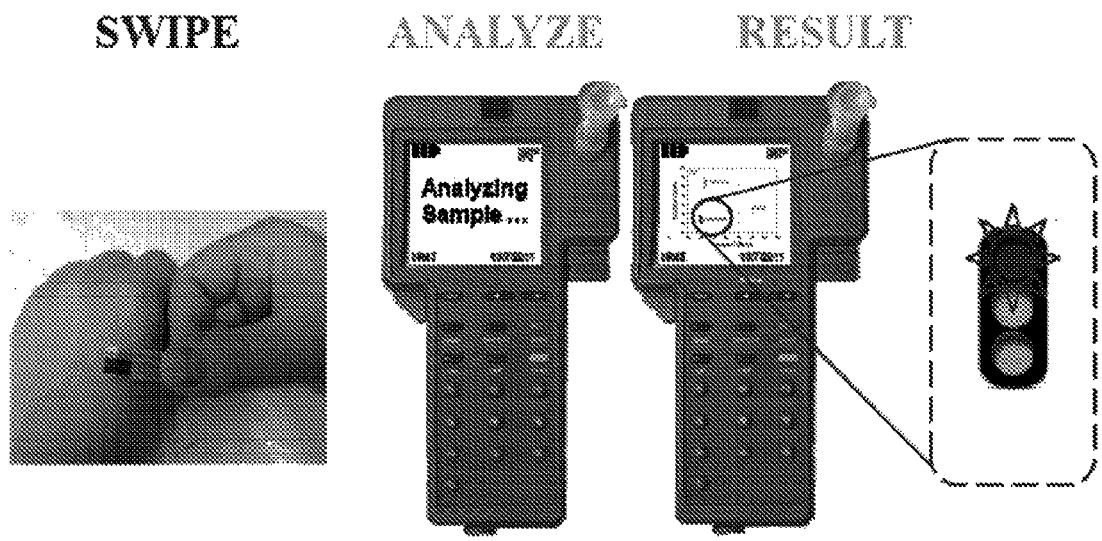
FIG. 1D shows an exemplary illustration of a chemometric technique to swipe, scan, and analyze a sample to identify chemical agents of interest and determine a level of exposure of the sample to the chemical agent using the portable device.

In some implementations of the system 110, for example, the data processing unit 112 can be configured to determine a level of exposure of the sample to the chemical agent by generating a series of coefficients of the electrochemical spectral signature to compress the data, e.g., using DWT or FFT, and classifying the chemical information based on the series of coefficients among preselected data sets to determine the level of exposure to the chemical agent. For example, the data processing unit 112 can classify the chemical information by performing pattern recognition using the preselected data sets and the series of coefficients of the electrochemical spectral signature to maximize inter-group variance between unique groups and minimize intra-group variance for a determination of a group or ranking to assign the chemical information. In some implementations of the system 110, the electrochemical analysis unit 111 and data processing unit 112 are both configured in a portable device to identify the chemical agent and determine the level of exposure of the sample to the chemical agent. In some implementations, for example, the system 110 can further include a remote computer in communication with the portable device via a communication network or link to receive the processed data including the classified chemical information from the portable device and to process the classified chemical information in a data library of previously collected samples. FIG. 1D shows an exemplary illustration of the chemometric technique to swipe, scan, and analyze a sample to identify chemical agents of interest and determine a level of exposure of the sample to the chemical agent using the portable device including the electrochemical analysis unit 111 and the data processing unit 112 with the electrode strip 100. For example, the portable device can be deployable in the field of use to provide a chemometric analysis in a matter of minutes. In some implementations, for example, the electrochemical analysis unit 111 is configured in a portable device and the data processing unit 112 is configured in a remote computer, in which the portable device includes a processor and memory unit coupled to the electrochemical analysis unit 111, and a transmitter unit to transmit the transduced electrical signal as transmitted data to the remote computer, and in which the remote computer is in communication with the portable device via a communication network or link to receive the transmitted data and process the transmitted data to identify the chemical agent and determine the level of exposure of the sample to the chemical agent.

The rapid detection of gunshot residues from an individual suspected of discharging or handling a firearm can provide valuable information in a multitude of scenarios in forensic investigations. Data from the Criminal Justice Statistics Center of the California Department of Justice show that over a 10 year period (1994-2004), firearms were the most commonly used weapon in homicide cases, constituting 72.6% of the weapons used. This level of firearm-related crime necessitates more forensic analysis of physical evidence in conjunction with police investigations.

Conventional forensic analysis systems use various analytical techniques for detection of both organic and inorganic constituents of GSR using a variety of analytical techniques. However, conventional methods for chemical analysis used are bulky, expensive, and require trained personnel operating within the confines of centralized laboratory facilities. For example, using such conventional methods requires that the sample be isolated and transported to the laboratory, which is a potentially deleterious proposition owing to the high likelihood of contamination during the sample transport process. For example, these conventional laboratory-confined analytical techniques include electrochemical analysis, gas/liquid chromatography, ion mobility, mass spectrometry, scanning electron microscopy, Raman spectroscopy, fluorescence spectroscopy, UV/VIS spectroscopy, and IR spectroscopy. Statistical processing on the collected data may subsequently be performed to qualify/quantify the results in order to yield a basic assessment of the presence of the analyte(s) of interest. Some techniques using voltammetry and PCA, for example, are capable of discriminating the type of firearm used by a suspect. However, unlike the disclosed technology, these existing techniques are incapable of providing sufficient specificity for the determination of whether or not a suspect has discharged a firearm or was merely in the proximity of such an event, e.g., including those with secondary contact with GSR. Moreover, such techniques are not amenable to field-deployment, thereby precluding applications requiring real-time, quasi-real-time, or on-the-spot/scene assessment.

Also, for example, GSR is currently analyzed by isolating small samples of clothing that are obtained from the suspect and examining these samples under an electron microscope for evidence of metallic particles originating from vaporized residue generated during discharge of the ammunition. This sampling technique is not capable of identifying individuals who may have handled ammunition or been in the vicinity of the discharge event, e.g., who could provide valuable information identifying culpability in criminal justice scenarios. Under the current state-of-the-art, many witnesses are released from questioning as current techniques fail to properly identify such individuals in the field, hence law enforcement is left to rely on word-of-mouth accounts and eye-witnesses, which often constitutes unreliable testimony. Moreover, the lack of technologies that facilitate the identification of those individuals present at the crime scene, irrespective of on-the-scene testimony, implies that crucial witnesses can simply be released without providing useful insight into a crime they might have witnessed or had direct involvement in. The disclosed technology is capable to provide law enforcement with an invaluable tool that will enable them to administer justice with substantially greater confidence and reliability.

I. Exemplary Implementations Using Voltammetric Electrochemical Sensing and Discriminant Function Analysis Data Processing Techniques Exemplary implementations of the disclosed chemometric systems, devices, and techniques are described that demonstrate the effective discrimination of different control scenarios for the determination of levels of contact with gunshot residue from the hands of different subjects. In some examples, electrochemical signals were detected and examined by maximizing variations in the signals generated by multiple organic and inorganic GSR constituents from subjects who have discharged a firearm, as compared with those who have had secondary contact with GSR (e.g., in the presence of other shooters or contact with GSR-contaminated surfaces). The exemplary implementations provide results showing that the disclosed technology can successfully address the key challenge of minimizing the false positive identification of individuals suspected of discharging a firearm.

In the described exemplary implementations, for example, voltammetric data was acquired from different control scenarios and processed using exemplary analysis techniques of the disclosed technology including Discriminant Function Analysis (DFA) to provide several distinct clusters for each scenario examined. DFA is also referred to as Canonical Variate Analysis (CVA). The exemplary implementations included use of exemplary field-deployable electrochemical stripping devices with the exemplary DFA data processing/clustering strategy. Multiple samples were taken from subjects under controlled conditions, e.g., such as secondary contact with GSR, loading a firearm, and post-discharge of a firearm. For example, cyclic square-wave voltammetry of samples taken from subjects in the different control scenarios were examined over a wide cathodic and anodic potential window, covering the redox processes of multiple organic and inorganic constituents of GSR. For example, the disclosed technology is capable of simultaneous electrochemical detection of both metallic and organic species consistent with GSR using a single electrode contingent in a single voltammetric run, which can be processed using the disclosed chemometric data processing techniques to enhance the information content and reliability of forensic GSR investigations. The exemplary controls were examined at both bare carbon and gold-modified screen-printed electrodes using different sampling methods, e.g., including a 'swipe' method of the present technology with integrated sampling and electroanalysis, and a traditional acid-assisted Q-tip swabbing method. The electroanalytical fingerprint of each sample was examined using square-wave voltammetry, and the resulting data were processed with Fast Fourier Transform (FFT), followed by the DFA treatment. In the exemplary implementations using the disclosed techniques, high levels of discrimination were achieved in each case over three classes of samples that reflected different levels of user involvement with the GSR, e.g., thereby achieving maximum accuracy, sensitivity, and specificity values of 100% employing the 'leave-one-out' validation method. Further validation with the 'jack-knife' technique was performed and the resulting values were in good agreement with the former exemplary method. Additionally, blind samples from subjects in daily contact with relevant metallic constituents were analyzed to assess possible false positives.

In the described exemplary implementations, the disclosed technology combines such information-enhanced electrochemical analysis with powerful multivariate DFA data processing to obtain effective and rapid discrimination between subjects who have discharged a firearm and those who have not under a variety of relevant control scenarios. The described DFA analysis techniques of the disclosed technology were used to classify samples from each control set, from two different points of view. This outlines a distinction between those who have had no contact with GSR, those who have had contact, albeit of the secondary form, and those who have directly handled a firearm, regardless of discharge within this implementation. Consistent DFA discrimination—with well-defined minimally-dispersed clusters—is thus illustrated for several different control signals taken before and after the discharge of the firearm for each subject examined herein. Such distinction may hold considerable importance in many applications to discriminate between direct involvement in a firearm-related crime or the mere presence in the vicinity of the discharge of a firearm.

In these exemplary implementations using the voltammetric/DFA discrimination techniques, two different sampling methods were used to obtain the gunshot residue for analysis. One of the exemplary sample collection methods involved a simple and fast integrated sampling/measurement 'swipe' method. For example, the use of disposable carbon sensor strips in this exemplary sample collection method ensures that a low cost and reliable electrochemical fingerprint is obtained from the firearm discharge samples compared to expensive, cumbersome laboratory equipment. Additionally, a traditional GSR sampling method was used involving dilute acid-assisted Q-tip swabbing for comparison.

I.1. Exemplary Materials and Methods

Exemplary chemicals and materials used in the described exemplary implementations included acetate buffer (pH 4.6), gold plating solution (e.g., $KAuCN_2$, ORO Temp24 RTU RACK), and deionized water (e.g., 18 MΩ-cm), which was used to prepare solutions.

Electrochemical measurements were performed using an μAutolab II (e.g., Eco Chemie, The Netherlands). Screen printed carbon electrodes (SPCEs) were used for the exemplary measurements. The carbon ink used for the working and counter electrodes was Acheson Electrodag 440B (Henkel Electronic Materials LLC). Au-modified SPCEs were modified using the gold plating solution ($KAuCN_2$).

Cyclic square wave voltammetry (SWV) was employed to characterize GSR electrochemical signatures. Square wave voltammetry is a large-amplitude differential technique in which a waveform composed of a symmetrical square wave, superimposed on a base staircase potential, is applied to the working electrode. The current is sampled twice during each square-wave cycle, once at the end of the forward pulse and once at the end of the reverse pulse. For example, at bare carbon SPCEs, oxidative SWV signals were obtained with an initial potential of −1.3 V vs. Ag/AgCl, maintained for 120 s, and subsequently scanned to a final potential of +1.3 V vs. Ag/AgCl. Reductive signals were implemented from initial potential 1.3 V (vs. Ag/AgCl), maintained for 120 s, and subsequently scanned to a final potential −1.3 V. At Au-modified electrodes, oxidative SWV signals were obtained with an initial potential of −0.8 V vs. Ag/AgCl, maintained for 120 s, and subsequently scanned to a final potential of +0.3 V vs. Ag/AgCl. The exemplary scans were performed at a frequency of 25 Hz, amplitude of 25 mV, and potential step of 4 mV, and the implementations were conducted in acetate buffer (pH 4.6).

I.2. Sampling of Gunshot Residue

Integrated sampling of GSR directly from the hand of a shooter was performed at a local shooting range using swiping sampling and swabbing sampling techniques.

Swiping samples were isolated by abrasively rubbing the electrode surface over the hand of the suspect. The sensor strip electrode was held at the silver electrical contacts by the sampler. Two types of swiping samples were taken: (a) the exemplary 3-electrode strip surface was swept over the back of the subject's firing hand 7 times; (b) from the thumb and back of the firing hand 5 times each. Each electrode was then placed in an individual resealable storage bag to prevent cross-contamination. For analysis, a 50 μL aliquot of acetate buffer was dropped onto the electrode surface (upon which the GSR sample has already been immobilized), and SWV was carried out as described above.

Swabbing samples were performed using a sample collection kit including plastic handled cotton tipped swabs, 2 mL glass sample vials, and a 5% (v/v) $HNO_3$ solution in a squeeze bottle. The GSR sample was collected by soaking the cotton tipped swab with 3 to 5 drops of the $HNO_3$ solution and swabbing the back of the hand. The cotton tip was then cut from the stem with scissors and placed in the glass vial. 1.00 mL of 4 M HCl/0.1 M acetate buffer was added to each sample. The samples were allowed to soak overnight (e.g., 12-16 hr) before analysis. For analysis, a 40 μL aliquot of acetate buffer was dispensed onto the electrode surface. The surface was then spiked with 10 μL of the GSR sample from the 4 M HCl/0.1 M acetate buffer mixture containing the cotton swab, and SWV was performed as described above.

For example, the sampling was not duplicated for any subject. Rather, comparison between samples from six different subjects per control scenario was deemed sufficient to demonstrate precision for these experiments.

For bare carbon SPEs, samples were obtained at different instances during the exemplary implementation process, e.g., (N) in the laboratory (prior to any contact with GSR), named N—No contact; (S) in the lobby of the shooting range, (without entering the lanes where others were discharging firearms), named S—Secondary contact; (P) at the shooting lanes where others were discharging firearms (without handling or discharge), named P—Presence at discharge; (L) having handled and loaded the firearm (without discharge), named L—Load; (F) after firing several rounds from the weapon (e.g., 10 rounds from a Glock 9 mm or 8 rounds for a Sig Sauer 45)—F—Fire; and (W) after washing the hands (with soap and water), named W—Wash. The six different subjects with six control scenarios resulted in 36 samples in total. These exemplary samples were obtained utilizing the swiping protocol (e.g., 36 samples) and the swabbing protocol (e.g., 35 samples due to an error in one of the samples).

For Au-modified SPEs, samples were obtained for four different subjects with five control scenarios (N—No contact, P—presence at discharge, L—Load, F—Fire, and W—Wash) utilizing the swiping protocol of sample collection. This resulted in a total of 20 samples. Voltammetry was conducted prior to the described implementations at the bare carbon SPE, fewer control scenarios and fewer subjects were involved. Subsequent to this data set, the exemplary method was enhanced with an additional control scenario (S—Secondary contact) and the number of subjects was increased to facilitate the DFA model.

The firearms used in the exemplary implementations included a Glock 17 9 mm and a Sig Sauer P220 45 caliber. The leaded ammunition used for the Glock was Remington UMC® Target 9 mm luger and the leadless ammunition was Remington UMC® 9 mm luger. The leaded ammunition used for the Sig Sauer was Remington UMC® Target 45 automatic.

I.3. Exemplary Data Processing Methods

Prior to building the exemplary classification model, a preprocessing step for data reduction was performed on the square-wave voltammograms obtained at the sensor strip electrodes, employing Fast Fourier Transform (FFT). In this manner, both the cathodic and the anodic waves of the SWV were compressed separately and a number of obtained coefficients were used as inputs in the classification model. Classification of samples was achieved by means of DFA analysis, which used a stepwise inclusion method to allow the removal of low-contributing variables to the classification model. Moreover, given that this is a supervised method, for example, classification success was evaluated using a 'leave-one-out' cross validation scheme. Additionally, to demonstrate, the efficacy of the disclosed methods, model classification success was further validated utilizing a 'jack-knife' method which, in turn, enabled the estimation of the associated standard errors. In the exemplary implementations, for example, chemometric processing of the data was performed by specific routines of the disclosed technology in MATLAB 7.1 (MathWorks, Natick, Mass.).

I.4. Exemplary Results of the Exemplary Implementations Using Voltammetric Electrochemical Sensing and DFA Data Processing Techniques The described exemplary implementations focused on the detection of GSR, obtained from the hand of a subject, over various control scenarios. The following sections demonstrate the unique classification protocol among subjects involved in the handling or discharge of a firearm as compared to subjects who have been in contact with gunshot residue from a secondary source. For example, voltammetric analysis was performed employing two types of sensor strip electrode and from samples collected using two separate methods (e.g., swiping and swabbing). This was followed by chemometric DFA treatment of the exemplary electrochemical data. Samples of GSR from different control scenarios were acquired and voltammetry was carried out as previously described. The voltammetric data were then preprocessed according to the FFT signal preprocessing described below. For example, this rapid and effective identification of subjects who have discharged a firearm, along with the control tests, make the development of the disclosed electrochemical/classification method promising for use in forensic investigations of firearm-related crimes.

I.4.1. Exemplary FFT Signal Preprocessing

For example, in the exemplary implementations, to fully exploit all the information obtained from each voltammogram and to prevent the saturation of the associated classification model with excessively complex data, a compression step was performed to decrease the dimensionality of the electrochemical signatures. In addition, for example, this step may also help to avoid redundancy in the input data and to obtain a more robust classification model with better generalization ability since high-frequency 'noise' is eliminated while preserving the 'signal' envelope. This exemplary compression step was achieved by means of a Fast Fourier Transform (FFT), which is particularly useful because of its ability to compress data and remove noise at the same time. In this way, compromising between the reconstruction degree and the number of obtained coefficients, raw voltammetric data was compressed up to only 64 coefficients without any loss of significant information, which allowed a compression of the original information up to 88.0% (e.g., 71.7% in the case of Au-modified electrodes). For example, although good representation of the original data could be achieved with fewer coefficients, e.g., increasing compression ratio, it was preferred to ensure the best reconstruction degree given DFA was performed using a stepwise inclusion method which allows for the removal of the variables that have a lower contribution to the classification model. That is, having a list of independent variables, some of which may be useful predictors, but some of which are almost certainly useless, the aim is to find the best subset to carry out the task of prediction as well as possible, with as few variables as possible. Hence, this method is very effective in selecting and removing the variables that do not contribute at all to the prediction success.

I.4.2. Exemplary Classification Models

DFA was used to classify samples from two different points of view for each set of samples. For example, in the first case, discrimination between the six types of samples (e.g., N—No contact, S—Secondary contact, P—Presence at discharge, L—Load, F—Fire, and W—Wash) was implemented. Also, for example, in the second case, discrimination of the samples was simplified to a 3-class study case (e.g., Free (N), Witness (S & P), and Involved (L, F & W)), outlining a subject's complicity in a firearm-related crime in a simpler manner. Although this entails a loss of information, for example, it can improve the reliability of the exemplary method. This outlines a distinction between those who have had no contact with GSR, those who have had contact, albeit secondary, and those who have directly handled the firearm, regardless of discharge. In particular, the exemplary control scenarios S—Secondary contact and P—Presence were, in part, chosen to reflect a subject in daily contact with GSR-constituent materials. Such distinction may hold much importance demonstrating implication in a crime as well as minimizing false positive identifications.

After pre-processing the recorded voltammograms with FFT, the obtained coefficients were used as input into the DFA model, which was employed to execute the classification of the samples. For example, given that this is a supervised method, classification success was evaluated using leave-one-out cross validation. For example, leave-one-out cross validation involves using a single observation from the original sample as the validation data, and the remaining observations as the training data. This can be repeated such that each observation in the sample is used once as the validation data. In this manner, each sample is classified by means of the analysis function derived from the other samples (all cases except the case itself). This process was repeated k times (as many as samples) leaving out one different sample each time, the one to be classified, which acts as model validation sample. Thus, with this approach all samples are used once as validation.

Upon completion of the DFA modelling, the 'jack-knife' method was used to evaluate the performance of the model. For example, the jack-knife method was originally suggested in statistical analysis as a general approach for testing hypotheses and calculating confidence intervals in situations where apparently no better methods could be used. With this exemplary approach, the samples were first split into training and testing subsets, then a model was constructed with data from the training subset, and its performance was evaluated using testing subset. Standard errors were calculated from different data subdivisions of training and test subsets with random distribution and repeating the modelling stage. In this manner, it may be implemented via either excluding one sample, or even several samples, during each iteration. This exemplary method has the advantage that it avoids dependence on predictions from the specific subdivision of data, e.g., thus providing a more realistic evaluation of the disclosed approach given that, in each case, a new model is trained and evaluated with a new external test subset of samples which are not employed in any way in the modelling routine. The 'goodness' of fit is, accordingly, a valid measure of the modelling performance. In this way, train/test data subdivision is repeated randomly k times, evaluating the model's response for the test validation subset during each iteration and using unbiased data.

In the exemplary case, the 'jack-knife' method was applied, e.g., training with 80% of the data and tested with the remaining 20%. For example, this subdivision of the original data set was subsequently repeated 10 times, excluding different test samples during each iteration. For example, each excluded sample was selected randomly to ensure the veracity of the model as well as to guarantee that performance does not depend on the specific subsets used. Finally, for example, model performance was evaluated from the mean of the replica results, which, in turn, allows for the calculation of the precision and confidence intervals for the obtained results.

I.4.3. Exemplary Results from SPCE Swipe

In the exemplary implementations, a bare SPCE was used to measure the organic and inorganic species present in GSR over a wide potential window. Samples taken from both the thumb and back of the hand were examined, as well as the back of the hand only. A clearer discrimination profile was obtained from these samples taken from the thumb and back of the hand. It is noted that clear discrimination from the samples taken from the back of the hand only were also achieved, with sensitivity and specificity values noted below. Both the oxidation and reduction profiles of the GSR samples were examined. One exemplary advantage of this method is to extract additional information of the anodic and cathodic signatures of other GSR components, e.g., such as organic compounds and other metals at more negative potentials, which can lead to a richer departure point, improving the model response and resulting in a less expensive sensor. In the course of the exemplary implementations, the voltammetry data from six subjects for the six different control scenarios (e.g., 36 samples) were analyzed.

Figure 2A:
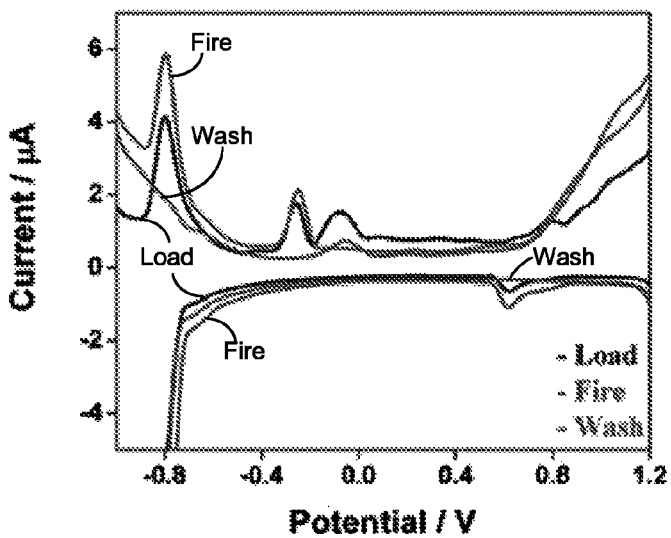
FIG. 2A shows a plot of exemplary different cyclic square-wave stripping voltammetric signals obtained with swiping samples at a bare screen printed carbon electrode (SPCE).

FIG. 2A shows a plot of an example of the different cyclic square-wave stripping voltammetric signals obtained from the subjects using the firearms and ammunition previously described by "swiping" samples at a bare SPCE electrode.

The exemplary voltammetry plot of FIG. 2A shows the samples for L—Load, F—Fire, and W—Wash data. For example, acetate buffer was dispensed onto the electrode surface subsequent to sampling and SWV was carried out in the potential range of −1.3 V to +1.3 V vs. Ag/AgCl. The oxidative voltammetry exhibits three stripping signals at potentials −0.8 V, −0.275 V and 0 V vs. Ag/AgCl. These can be attributed to anodic stripping of metals, e.g., zinc+nickel amalgams, lead and copper, respectively. The signals for lead and copper and for nickel-zinc alloys are observed at similar potentials at a glassy carbon electrode (GCE). Each of these species is noted to be present in the ammunition according to the material safety data sheets. The signal at 0 V (vs. Ag/AgCl) is much greater for the L—Load scan than it is for any of the other scans. For example, this signal can be attributed to Cu, and the increase in the signal for the L-scan may be attributed to increased contact of Cu from the brass bullet case. This electrochemical behavior was observed using the 'swipe' method of GSR collection. Further signals are observed at more positive potentials also, for example, which may be attributed to the organic components of GSR. Anodic signals are observed at 0.25 V, 0.6 V, and 1.098 V (vs. Ag/AgCl). For example, these may be attributed to oxidation of diphenyl benzene (DPB), diphenylamine (DPA) and nitroglycerin (NG), respectively. Both DPA and NG are noted to be present in all the ammunition according to the material safety data sheet and DPB is formed upon the oxidation of DPA. The signals for these species are observed at similar potentials at a GCE during investigations of the metallic and organic constituents of GSR. Upon the cathodic sweep of the GSR samples, a signal was observed in the F—Firing scan at a potential of 0.625 vs. Ag/AgCl, which may be attributed to the reduction of DPA. The exemplary implementations of this cyclic SWV waveform were used to deliver such a detailed electroanalytical fingerprint, in a single voltammetric run, e.g., which demonstrates the intrinsic advantages of simplicity and rapidity of the disclosed methods for the detection of the components of GSR.

Figure 2B:
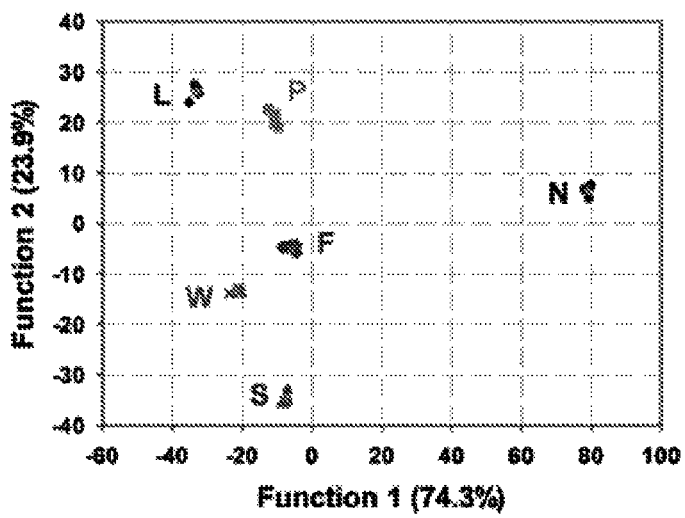
FIGS. 2B and 2C show score plots of the functions produced after Discriminant Function Analysis (DFA) of exemplary gunshot residue (GSR) samples obtained by SPCE swiping according to exposure level and 3-class response mode, respectively.
Figure 2C:
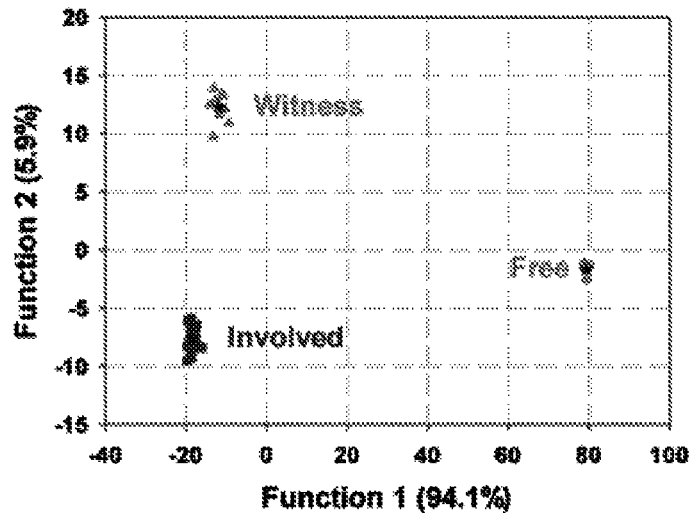

FIGS. 2B and 2C shows score plots of the functions produced after DFA analysis of the GSR samples according to exposure level (FIG. 2B) or 3-class response mode (FIG. 2C). The exemplary samples in the plot of FIG. 2B correspond to N—No contact, S—Secondary contact, P—Presence at discharge, L—Load, F—Fire, and W—Wash. The exemplary samples in the plot of FIG. 2C correspond to Free (N), Witness (S & P), and Involved (L, F & W).

For example, FIG. 2B shows clear discrimination of the samples was achieved at these electrodes upon DFA treatment of this data, with patterns in the score plot evidencing that samples are grouped according to the exposition level (level of exposure). The score plot of FIG. 2B shows well-established clusters clearly separated for the six classes of samples. The exemplary classification results of the DFA leave-one-out cross validation technique are summarized in Table 1.

Table 1 shows an example of a confusion matrix built according to GSR exposure level obtained using the exemplary GSR sample acquisition techniques and the exemplary DFA model and leave-one-out cross validation for the exemplary three set of samples: a: swipe SPCE; b: swab SPCE; and c: gold-modified SPCE.

TABLE 1

| | Found | | | | | | | | | | | | | | | | | |
|---|---|---|---|---|---|---|---|---|---|---|---|---|---|---|---|---|---|---|
| | N | | | S | | | P | | | L | | | F | | | W | | |
| Expected | a | b | c | a | b | c | a | b | c | a | b | c | a | b | c | a | b | c |
| N | 6 | 6 | 6 | 0 | 0 | 0 | 0 | 0 | — | 0 | 0 | 0 | 0 | 0 | 0 | 0 | 0 | 0 |
| S | 0 | 0 | 0 | 5 | 5 | 2 | 0 | 0 | — | 0 | 1 | 0 | 0 | 0 | 0 | 1 | 0 | 0 |
| P | 0 | 0 | 0 | 0 | 0 | — | 6 | 4 | — | 0 | 1 | — | 0 | 1 | — | 0 | 0 | — |
| L | 0 | 0 | 0 | 0 | 0 | 0 | 2 | 1 | — | 4 | 4 | 4 | 0 | 0 | 0 | 0 | 0 | 0 |
| F | 0 | 0 | 0 | 0 | 1 | 0 | 0 | 0 | — | 0 | 1 | 0 | 6 | 2 | 4 | 0 | 2 | 0 |
| W | 0 | 0 | 0 | 0 | 0 | 2 | 0 | 0 | — | 1 | 0 | 0 | 1 | 0 | 0 | 4 | 6 | 2 |

As shown in the Table 1 and the DFA plot of FIG. 2B, nearly all samples were correctly classified according to exposure level. For example, the classification rate of the samples in this exemplary implementation reached an accuracy of 86.1%. The efficiency of the exemplary classification produced was also evaluated according to its sensitivity, e.g., the percentage of objects of each class identified by the classifier model, and to its specificity, the percentage of objects from different classes correctly rejected by the classifier model. The value of sensitivity, averaged for the classes considered was 86.1%, and that of specificity was 97.2%. Thus, the exemplary method provides clear discrimination of various control scenarios for a number of subjects over a very short timescale with facile sampling and analysis. For example, DFA was also performed on samples taken using the swiping method from the back of the hand only and resulted in a classification rate 66.7%, sensitivity of 66.7% and specificity of 93.3%.

For example, to enhance model reliability and further provide a simpler response outlining a subject's complicity, classification of samples was also implemented by shrinking previous data to a 3-class study case. As per FIG. 2B, a new exemplary DFA model was built and evaluated using the leave-one-out cross validation method. In this exemplary case, only three groups were considered, Free, Witness and Involved, and the exemplary DFA model was formed by just two discriminant functions (DFs). The same data used for FIG. 2B was also used in this exemplary model, whereby Free encompasses N—No contact, Witness uses the previous data for S—Secondary contact and P—Presence at discharge, and Involved uses the data for L—Load, F—Fire, and W—Wash.

For example, FIG. 2C shows clear discrimination for the samples based on the three exposure level categories. The patterns shown in the score plot of FIG. 2C evidence that samples are grouped according to degree of involvement. For example, according to this classification, the Free cluster is still far removed from the other two clusters, which have similar merits for DF1, but that are clearly separated by DF2. For example, similar behavior is observed for Witness and Involved, whereby no overlap with the other categories was observed and clear discrimination along the axes was obtained, e.g., providing a simple system for the discrimination of subjects in different scenarios based on their exposure to GSR. Furthermore, as with the previous case for the six categories (shown in FIG. 2B), a confusion matrix was constructed employing an exemplary leave-one-out cross validation technique, the results of which are summarized in Table 2.

Table 2 shows an example of a confusion matrix built according to the 3-class response mode produced using DFA model and leave-one-out cross validation for the exemplary three set of samples: a: swipe SPCE; b: swab SPCE; and c: gold-modified SPCE.

TABLE 2

| | Found | | | | | | | | |
|---|---|---|---|---|---|---|---|---|---|
| | Free | | | Witness | | | Involved | | |
| Expected | a | b | c | a | b | c | a | b | c |
| Free | 6 | 5 | 4 | 0 | 0 | 0 | 0 | 1 | 0 |
| Witness | 0 | 0 | 0 | 12 | 12 | 4 | 0 | 0 | 0 |
| Involved | 0 | 2 | 0 | 0 | 0 | 0 | 18 | 15 | 12 |

As shown in the Table 2 and the DFA plot of FIG. 2C, all of the exemplary samples were correctly classified, with a classification rate of 100% in terms of accuracy. Also the same values for sensitivity and specificity were obtained for the exemplary method. For example, it is noted that an interesting noticeable feature is the reduced dispersion on the attained grouping, especially in contrast with the high separation between groups. For example, this feature may constitute highly reliable decision systems, where 'no doubt' cases appear.

I.4.4. Exemplary Results from SPCE Swab

Swabbing assisted with diluted acid is traditionally used to obtain GSR samples from a subject suspected of discharging a firearm for electroanalysis. The exemplary implementations of the disclosed chemometric technology includes a new DFA model to assess the discrimination capabilities when swabbing was utilized as an exemplary method to obtain GSR samples from a suspect. These samples were also measured at bare SPCEs. In the course of these exemplary implementations, the data from the subjects for the different control scenarios (e.g., 35 samples) were analyzed.

Figure 3A:
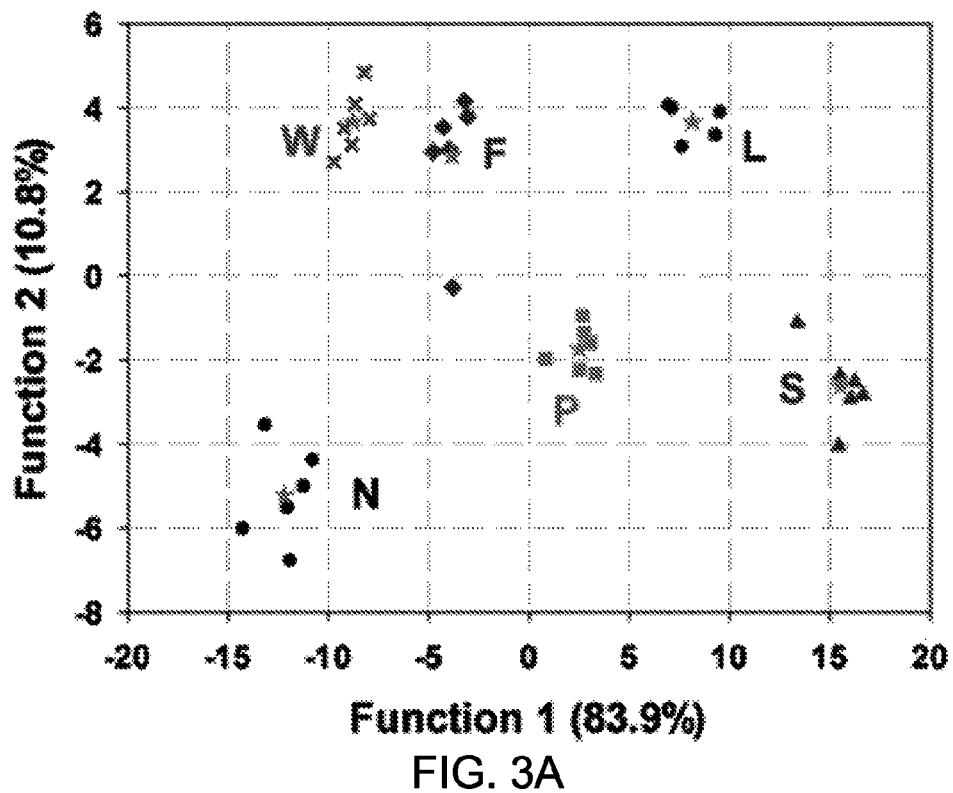
FIGS. 3A and 3B show score plots of the functions produced after analysis of exemplary GSR samples obtained by SPCE swabbing according to exposure level and 3-class response mode, respectively.
Figure 3B:
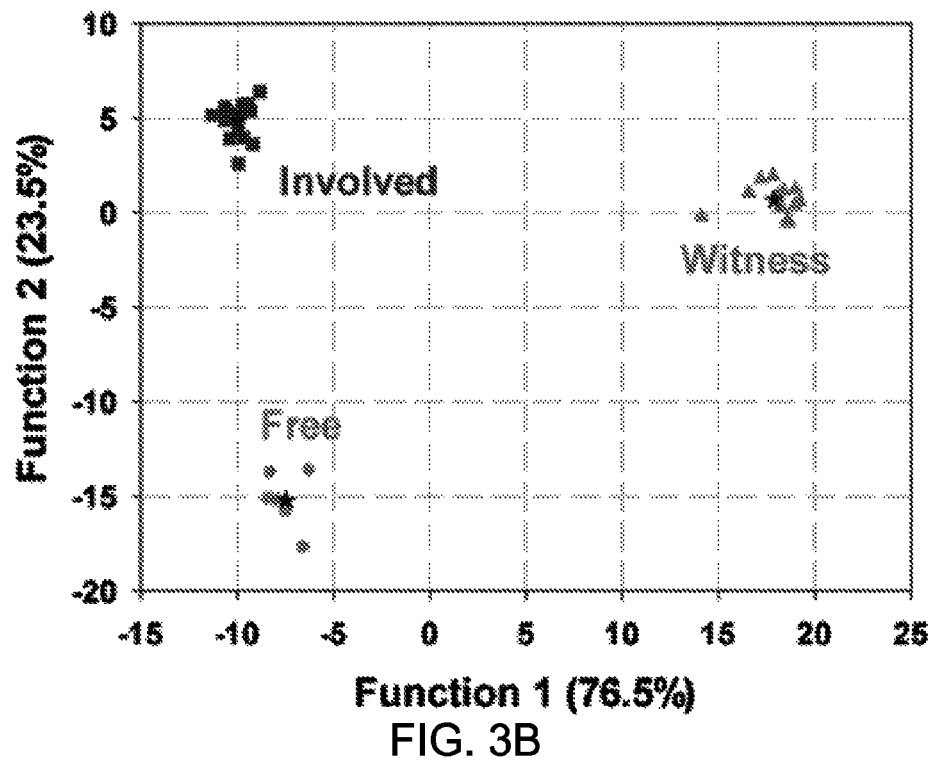

FIGS. 3A and 3B show score plots of the functions produced after DFA analysis of the exemplary GSR samples obtained by SPCE swabbing according to exposure level and 3-class response mode, respectively. The exemplary GSR samples correspond to the same controls outlined in FIGS. 2B and 2C. It is noted, for example, as shown in the data plots of FIGS. 3A and 3B, larger dispersion along cluster centroids was observed, e.g., as compared to the 'swiping' procedure of FIGS. 2B and 2C, although discrimination for all the classes is still achieved.

FIG. 3A shows the score plot of the first two discriminant functions obtained after DFA analysis of GSR samples according to six classes observed in FIG. 2B (e.g., N—No contact, S—Secondary contact, P—Presence at discharge, L—Load, F—Fire, and W—Wash). As shown in FIG. 3A, it was observed that N—No contact samples appear further from the other classes, but not by as much as in previous cases of the exemplary implementations using the 'swiping' method of sample collection. That is, for example, N—No contact samples have lower DF2 score values; P—Presence and S—Secondary contact samples have similar intermediate DF2 score values, being discriminated by DF1; and W—Wash, F—Fire and L—Load samples present the same behavior. FIG. 3B displays the classification of swabbing samples according to a simpler response mode observed in FIG. 2C (e.g., Free (N), Witness (S & P), and Involved (L, F & W)). As shown in FIG. 3B, the data plot shows less dispersion along the centroids. For example, for the groups sorted according to exposure level along DF2, the exemplary Free group is further from the others, and Involved and Witness groups are mainly separated by DF1.

For example, a confusion matrix was built employing the exemplary leave-one-out cross validation approach for both cases, with results provided in Table 1 (for FIG. 3A) and Table 2 (for FIG. 3B). For the exemplary implementations of the six classes study case (FIG. 3A, Table 1), as shown in the DFA plot, predictive performance was lower than that achieved for the 'swiping' method of sample collection, with a classification rate of 77.1% in terms of accuracy. Also, for example, the exemplary implementations for the swabbing method resulted in the model's sensitivity and specificity being demoted, e.g., with values of 77.2% and 95.5%, respectively. However, in the case of the 3-class study, as shown in FIG. 3B and Table 2, better results were obtained with a classification rate of 91.4%, sensitivity of 90.5% and 95.8% for specificity.

The exemplary classification method can be useful for field-deployable applications for identification of involvement in a crime, as it displays higher values of sensitivity and specificity regardless of the sampling method, as demonstrated in the exemplary implementations. Although, it was shown that the 'swiping' method of sample collection provides higher discrimination than that of the 'swabbing' method. For example, this can be highly advantageous, as the swiping technique is cheaper and faster than the swabbing technique, as well as more suited to in-field sampling and analysis by minimally-trained operators.

I.4.5. Exemplary Results from AuSPCE Swipe

The exemplary implementations included comparing the bare SPCE electrodes with those previously obtained employing gold-modified electrodes. In this exemplary case, samples were taken from four subjects in the following five exemplary scenarios: N—No Contact, P—Presence at discharge, L—Load, F—Fire, and W—Wash (e.g., resulting in 20 samples in total). Based on the exemplary results gathered and following the same exemplary procedure for data treatment, new models were built, and the exemplary results that were obtained are presented in FIGS. 4A and 4B.

Figure 4A:
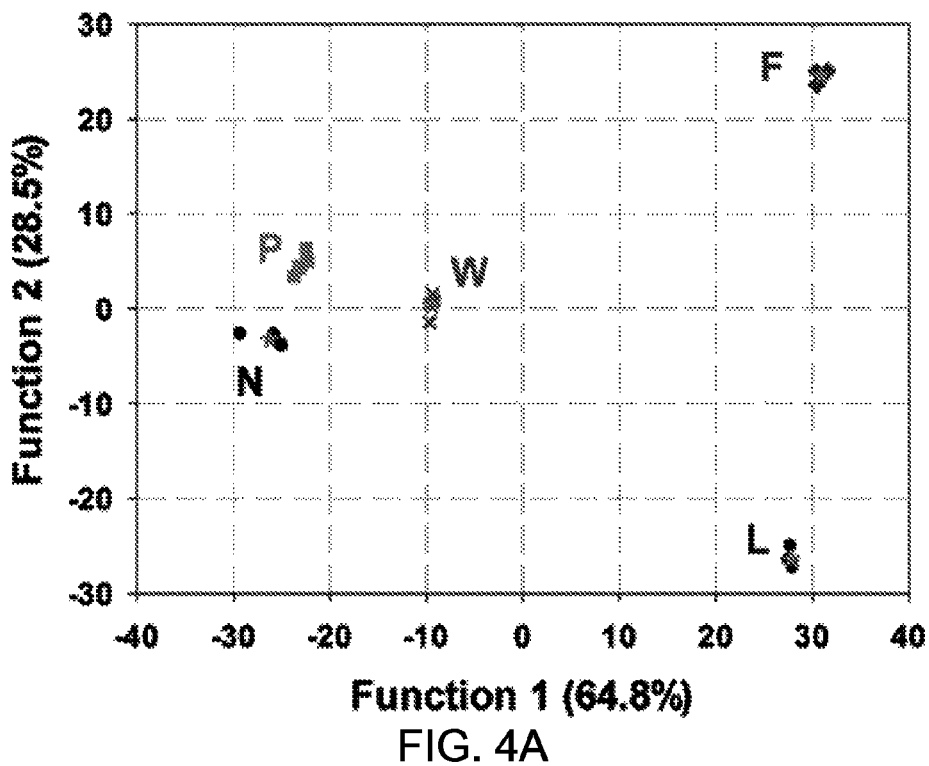
FIGS. 4A and 4B show score plots of the functions produced after analysis of exemplary GSR samples obtained by gold-SPCE swiping according to exposure level and 3-class response mode, respectively.
Figure 4B:
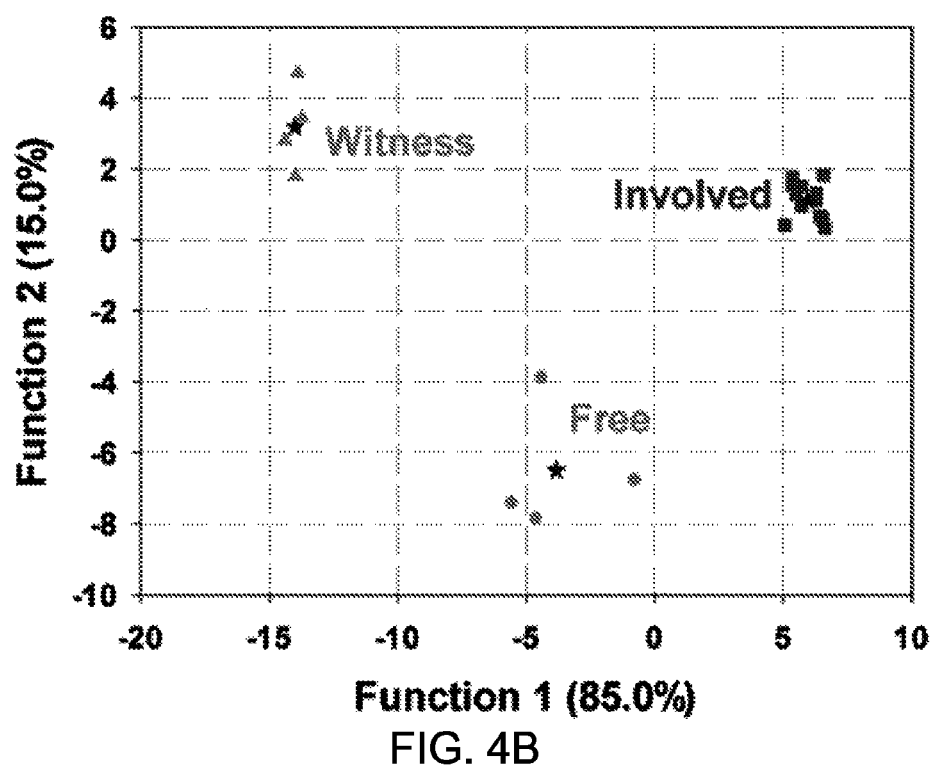

FIGS. 4A and 4B show score plots of the functions produced after analysis of exemplary GSR samples obtained by gold-SPCE swiping according to exposure level and 3-class response mode, respectively. The samples in the score plot of FIG. 4A correspond to: N—No Contact, P—Presence at discharge, L—Load, F—Fire, and W—Wash. The samples in the score plot of FIG. 4B correspond to: Free (N), Witness (P), and Involved (L, F & W).

FIG. 4A displays analysis from the five different scenarios mentioned above and demonstrates clear discrimination obtained between the different types of samples, with well-established clusters for each of the expected classes and low dispersion along each class centroid. As shown in the data plot, the sample clusters are sorted along DF1 based on the exposure level to GSR. For example, that is, moving along the 'Function 1' axis from left to right, a trend is shown based on the exposure to GSR from No Contact to Fire, relating position/score with the exposition level. Meanwhile DF2 mostly discriminates load and fire clusters from the rest. It is noted that, in the exemplary implementations, Wash samples have intermediate score values between classes with less exposure (No Contact or Presence at discharge) and those with higher exposure (Load and Fire), for example, which may be expected from deliberate removal of a significant degree of GSR from the hands of the subjects. Even under such scenarios, it is still possible to distinguish the cases with use of the exemplary model. The confusion matrix was built and predictive evaluator's indexes were extracted (as shown in Table 1). In this exemplary case, the classification rate reached 80.0%, sensitivity was 80.0%, and specificity was 95.0%.

For example, to further enhance the exemplary model's response and increase classification rate, a new exemplary model based on three classes similar to those observed in FIGS. 2C and 3B, was built, as shown in FIG. 4B. The score plot of FIG. 4B shows clear discrimination for the samples Free (N), Witness (P), and Involved (L, F & W) based on the three exposure level categories. The exemplary patterns in the score plot evidence that the samples are grouped according to degree of involvement. Moreover, for example, the exemplary samples can be distinguished by only the scores of DF1, where DF2 mainly separates Free from Witness and Involved clusters, which share more similarities. In this way, using the new samples division (shown in Table 2), the classification rate improved to 100%, with the same values obtained for the method's sensitivity and specificity.

The exemplary classification method shown in FIGS. 4A and 4B can be advantageous in the field for identification of involvement in a crime as it displays higher values of sensitivity and specificity regardless of either the electrode surface used or the sampling method implemented. This particular classification system can also allow for a simpler, more robust portable electronic system whereby facile responses to only three classes can be obtained, for example, rather than the six classes outlined. This exemplary approach can also involve the simplification of the Free and Witness categories into one category, in some implementations, for example, which can ensure that those in daily contact with GSR-constituent species are not implicated.

I.4.6. Exemplary Implementations for Minimization of False Positive Identification of a Shooter Exemplary implementations of the disclosed chemometric systems, devices, and methods were further conducted to demonstrate efficacy in preventing false positive identification occurrences. For example, in these exemplary implementations, voltammetric signature and resulting chemometric data generated from samples taken from machine-shop technicians and smokers were examined. The machine-shop technicians were selected as they would be in contact with metals consistent with GSR through daily activities such as operating heavy machinery, painting, milling, and welding. Smokers were selected to observe whether there would be any similarities between the organic species found in cigarette smoke and gunshot residue. The samples were obtained from the thumb and back of the hand of the subject using the swiping method. The samples were examined using square-wave voltammetry, and the data were processed and inputted into the previously-implemented model reported in FIG. 2B. For example, the exemplary samples did not contribute to the training process and were considered as blind samples for the exemplary model.

Figure 5:
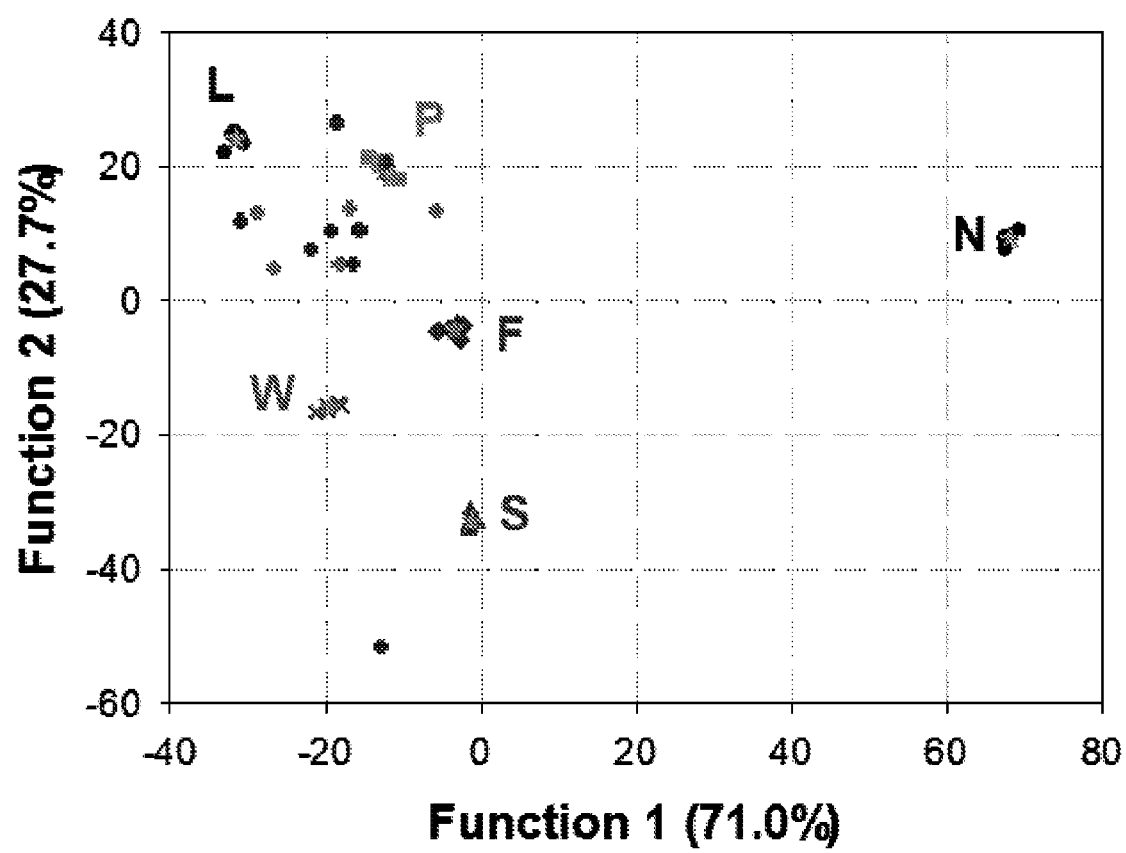
FIG. 5 shows a score plot of the functions produced after analysis of exemplary GSR samples according to exposure level.

FIG. 5 shows a score plot of the functions obtained after DFA analysis of the GSR samples according to the exposure level outlined in FIG. 2B. Data points corresponding to the machine shop technicians are shown with a purple (+), and data points corresponding to the smokers are shown with a grey (+). The exemplary implementation produced exemplary results in which, of the twelve samples taken (e.g., 7 technicians, 5 smokers), one was classified in S—Secondary contact, eight in P—Presence at discharge, and three in L—Load. While ideally all these samples would have been classified in N—No contact, it is not surprising that they are more consistent with samples taken after secondary contact from GSR-contaminated surfaces and GSR immobilized by other shooters. It is noteworthy that none of the subjects examined were classified as F—Fire.

I.4.7. Exemplary Implementations Using 'Jack-Knife' Validation

Although results produced using a leave-one-out strategy can be considered as overoptimistic, for example, but its implementation can be valuable when large sample sets are unavailable. In this respect, a second classification model was used in the exemplary implementations of the disclosed chemometric technology to process all of the data reported herein to demonstrate the efficacy of the disclosed method, which included using the jack-knife technique to facilitate the calculation of standard errors of the performance indicators.

With this exemplary approach, the samples are first split into training and testing subsets, then a model is constructed with data from the training subset and its performance is evaluated using testing subset. Thus, in this manner, data used to evaluate the model's performance is not used in its construction, hence facilitating the collection of unbiased and more realistic performance indicators. For example, this separation was performed at random, and the classification model was executed for 10 iterations using different samples for training and validation at each step to ensure that no bias was present. The exemplary results of the mean values for accuracy, sensitivity, and specificity for ten different models, for each data set reported, are shown in Table 3. For example, when comparing these exemplary values to those obtained using the leave-one-out approach, similar behavior is obtained, although the exemplary results are slightly demoted, e.g., given the variation in the train/test data proportion (e.g., fewer samples are used to build the model, which can decrease its generalization ability). However, the use of the exemplary jack-knife approach also allows the estimation of tolerance values for accuracy, sensitivity, and specificity percentages, e.g., providing additional information of the precision of the exemplary approach.

Table 3 shows an exemplary summary of the performance of the exemplary models for the different approaches employing both leave-one-out and jack-knife for the validation. In the jack-knife, for example, the exemplary results correspond to the mean and standard deviation of ten replicas.

the sampling and analysis through the 'swiping' method of sample collection provided a higher level of discrimination for the different scenarios, for example, as compared to the more traditional sampling method of swabbing, and thus can allow for a rapid and facile system for operatives in the field. The use of an exemplary bare carbon sensor strip for this analysis also provided an inexpensive and portable electrode surface. Also, for example, samples from subjects in occupations with daily exposure to materials consistent with GSR were also examined using the exemplary DFA model. None of these samples were classified as having fired a weapon, which may minimize false positive identification. The specificity, rapidity and portability of the disclosed chemometric technology make it capable for a field-deployable, hand-held device for investigating firearm-related

TABLE 3

|  | Leave-one-out | | | Jack-knife | | |
|---|---|---|---|---|---|---|
|  | % Class | Sensitivity | Specificity | % Class | Sensitivity | Specificity |
| CSPE/Swipe 6 classes | 86.1% | 86.1% | 97.2% | 85.7 ± 9.5% | 85.0 ± 10.2% | 97.2 ± 1.9% |
| CSPE/Swipe 3 classes | 100% | 100% | 100% | 95.7 ± 9.6% | 95.7 ± 9.6% | 95.7 ± 9.6% |
| CSPE/Swab 6 classes | 77.1% | 77.2% | 95.5% | 74.3 ± 13.1% | 74.3 ± 13.1% | 74.3 ± 13.1% |
| CSPE/Swab 3 classes | 91.4% | 90.5% | 95.8% | 90.0 ± 9.6% | 90.0 ± 9.6% | 90.0 ± 9.6% |
| Au-modified/Swipe 6 classes | 80.0% | 80.0% | 95.0% | 85.0 ± 12.9% | 85.0 ± 12.9% | 85.0 ± 12.9% |
| Au-modified/Swipe 3 classes | 100% | 100% | 100% | 95.0 ± 10.5% | 95.0 ± 10.5% | 95.0 ± 10.5% |

For example, the exemplary data in Table 3 demonstrates that the variations in the different control scenarios are sufficient to provide acceptable classification between a subject who has discharged a firearm and one who has not. In particular, for example, the values obtained for accuracy, sensitivity, and specificity for the preferred method of swiping at a bare carbon SPE using a 3-class system (Free, Witness, Involved) are 96%, 96% and 98%, respectively. This shows the robust nature of the GSR sensor strip, integration of the sampling protocol with the sensor strip towards efficient collection, and successful data reduction and feature extraction. For example, this second prediction set validates the EC/DFA relationship described herein for effective discrimination of GSR samples from relevant scenarios.

The described exemplary implementations have demonstrated the coupling of advanced electrochemical analysis with powerful multivariate classification analysis techniques for the rapid identification of a subject who has discharged a firearm utilizing a sensor strip electrode and integrating sampling and analysis. Effective discrimination of the level of contact with GSR for different subjects examined in these exemplary implementations has been achieved using a variety of control experiments relevant to various forensic scenarios, as indicated from the corresponding well-defined, minimally-dispersed clusters. Specifically, for example, the voltammetry of samples taken from subjects were examined in several control tests, e.g., including no exposure to GSR, secondary exposure from surfaces and air, and exposure from loading and firing. The results of the exemplary voltammetric/DFA analysis provided distinguishable clusters for each scenario examined, and the results of which were validated using two different approaches, e.g., the leave-one-out and jack-knife techniques. The integration of crimes that can decrease the occurrence of false positive identifications for the discharge of a firearm.

II. Exemplary Implementations Using Abrasive Stripping Voltammetry and Analysis

Exemplary implementations of the disclosed chemometric systems, devices, and techniques are described that demonstrate the rapid identification of chemical agents in GSR using field-deployable, on-the-spot detection tools. For example, in these exemplary implementations, a sampling and detection methodology is described that relies on abrasive stripping voltammetry involving an initial mechanical transfer of trace amounts of surface-confined GSR from the hand of a suspect directly onto the electrode contingent of the sensor strip (e.g., a screen printed electrochemical sensor), which is immediately ready for electrochemical analysis. Such integrated sampling/detection techniques can provide instant identification of a subject who has discharged a firearm, as well as the preservation of the sample integrity, e.g., minimizing errors associated with the transport and storage of samples.

Sampling and analysis are implemented using a protocol described here as abrasive stripping voltammetry (AbrSV) based on an initial mechanical transfer of trace amounts of the GSR from the hand of the suspect directly to the surface of the working-electrode sensor strip without intermediate processing steps. For example, using the present technology, application of the AbrSV technique can be implemented with anodic stripping voltammetry (ASV) for the detection of GSR samples at a screen-printed sensor strip, e.g., which can overcome existing limitations associated with the effective collection of residues and simplifying the overall electroanalytical protocol.

II.1. Exemplary Materials and Methods

Exemplary chemicals and materials used in the described exemplary implementations included acetate buffer (e.g., pH 4.6); standard solutions of copper, lead, and antimony; gold plating solution (e.g., $KAu(CN)_2$, ORO Temp24 RTU RACK, 7 g $L^{-1}$), and deionized water (e.g., 18 MΩ-cm), which was used to prepare solutions.

Electrochemical measurements were performed using an Autolab PGSTAT 12 (e.g., Eco Chemie, The Netherlands). Carbon screen-printed electrodes (CSPEs) were used for the exemplary measurements. The CSPEs were modified using $KAu(CN)_2$ (aq.) with an applied potential of −0.9V vs. Ag/AgCl and a charge of 8 mC. This modification allowed the separation of Sb and Cu signals in exemplary implementations which were not observed at the bare carbon. The peak potentials of Pb, Sb and Cu were first evaluated. Each metal (Sb, Pb, Cu) was sequentially spiked into buffer solution on the electrode surface to a concentration of 300 ppb from stock solutions.

Square wave voltammetry (SWV) was employed to characterize GSR electrochemical signatures. A potential of −0.8 V vs. Ag/AgCl was held for 120 s, and scanned to a final potential of +0.3 V vs. Ag/AgCl. An accumulation time was implemented for deposition of metals ions present in GSR alongside metallic species. The exemplary scans were performed at a frequency of 25 Hz, amplitude of 25 mV, and potential step of 4 mV and conducted in acetate buffer (e.g., pH 4.6).

II.2. Sampling of Gunshot Residue

Integrated sampling of GSR directly from the hand of a shooter was performed at a local shooting range. The samples were isolated by abrasively rubbing the exemplary 3-electrode strip surface (e.g., such as the electrode strip 100 of FIG. 1A) over the back of the firing hand five times from wrist to knuckle, and over the surface of the thumb five times from knuckle to tip. Each exemplary sample was taken by the same operator from four different subjects and placed in an individual polyethylene bag.

The exemplary samples were obtained at different instances during the implementation process, e.g., including (1) in the laboratory, prior to any contact with GSR, named C1: 1st Control; (2) at the shooting lanes where others were discharging firearms, but without handling or discharging a firearm, named C2: 2nd Control; (3) having handled and loaded the firearm, but without discharge, named L: Loading; (4) after discharging several rounds from the weapon (e.g., 10 rounds for a Glock 40 and 8 rounds for a Sig Sauer 45), named F: Firing; and (5) after washing the hands (e.g., with soap and water), named W: Wash. For example, the firearms used in this exemplary implementation included Glock 40 calibre with Fiocchi (40 Smith & Wesson) ammunition and Sig Sauer 45 caliber with PMC® Bronze (45 Auto) ammunition.

Figure 6A:
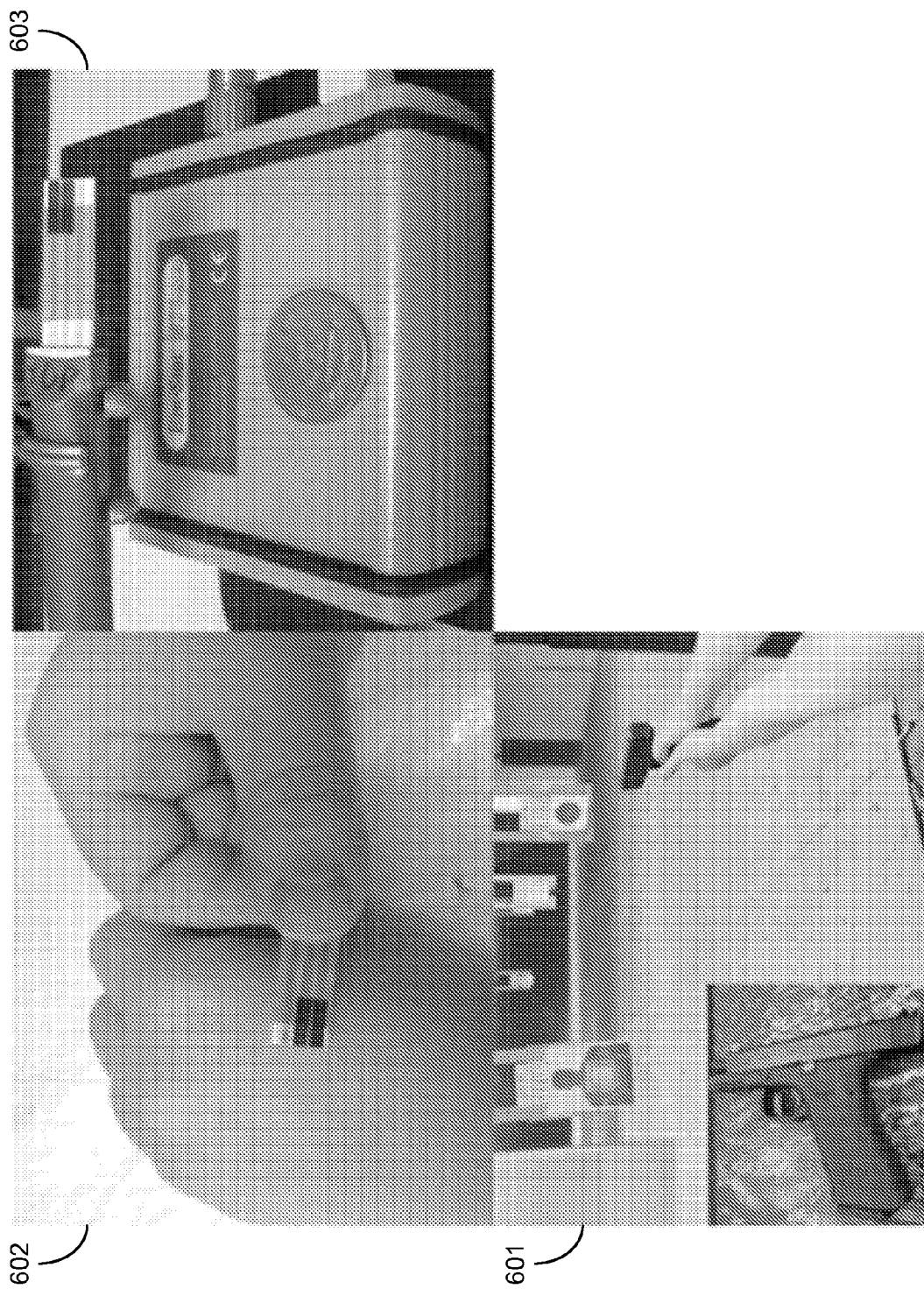
FIG. 6A shows a sequence of diagrams illustrating the exemplary 'swipe-and-scan' technique of the disclosed technology.

II.3. Exemplary Results of the Exemplary Implementations Using Abrasive Stripping Voltammetry and Analysis In the exemplary implementations of the AbrSV technique, an initial mechanical transfer of trace amounts of surface-confined GSR from the hand of a shooter was performed directly onto the electrode surface, without any intermediate swabs or potential contamination. FIG. 6A shows a sequence of diagrams illustrating the exemplary 'swipe-and-scan' technique of the disclosed technology. Diagram 601 shows an image of an exemplary subject discharging a firearm ('Shoot'). Diagram 602 shows an image of an exemplary sensor strip being rubbed over the subject's hand ('Swipe'). Diagram 603 shows an image of an exemplary electrochemical analyzing unit, in which buffer solution is dropped directly onto the electrode and the ASV technique is implemented ('Scan').

Figure 6B:
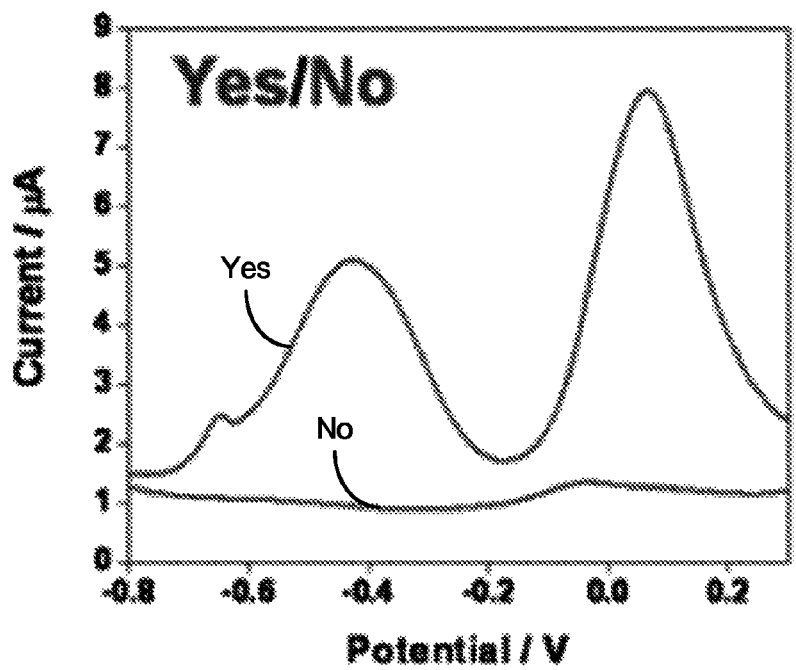
FIGS. 6B and 6C show a data plot of exemplary results produced by the exemplary 'swipe-and-scan' technique.
Figure 6C:
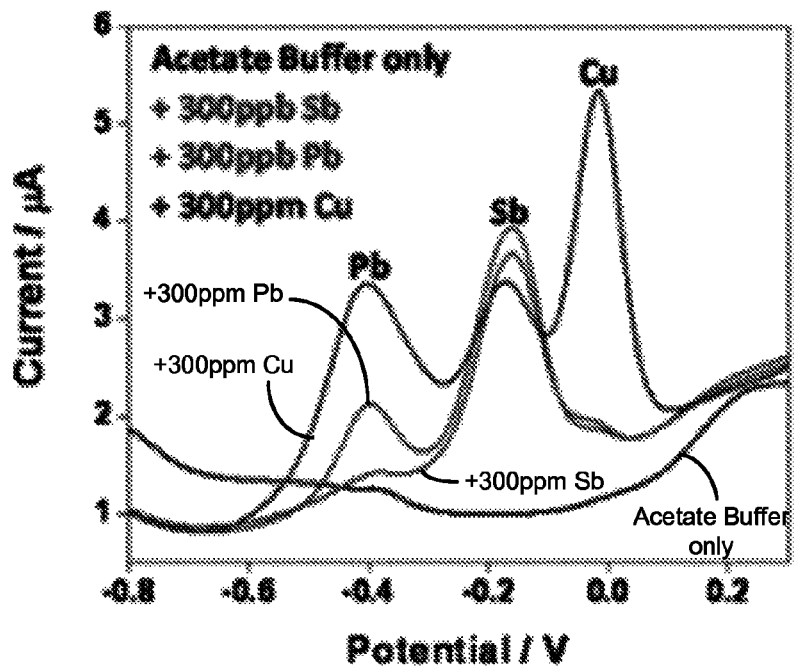

FIG. 6B shows a data plot of an exemplary output display showing the results obtained by the scan and swipe technique, in which one waveform represents a sample analysis without exposure to GSR (No) and another waveform represents a sample analysis including post-firearm discharge (Yes). For example, in the case of 'Yes', two voltammetric signals are observed. In this example, a signal at −400 mV vs. Ag/AgCl can be attributed to Pb, and the signal at 0 mV vs. Ag/AgCl can be attributed mainly to Cu, but with contributions from Sb. This exemplary signature can be compared to standard additions of Pb, Sb and Cu, e.g., examined at the Au-CSPE in buffer, as shown in the data plot of FIG. 6C. As shown in FIG. 6C, the exemplary standard comparison analysis yielded a signal for Pb at −400 mV, a signal for Sb at −50 mV and a signal for Cu at 0 mV vs. Ag/AgCl. In this example, a clear signal is not observed for Sb, e.g., which may be since levels of Sb in GSR are known to be significantly lower than both Pb and Cu. However, for example, contributions from Sb are indicated by the shift of the Cu peak potential to a more negative value. The exemplary implementation demonstrated that control signals taken before and after the discharge of the firearm and the resulting voltammetry analysis were consistent over the four subjects examined.

The exemplary implementations included the investigation of the effect of the exemplary AbrSV 'swipe-and-scan' technique for the detection of GSR before and after discharging a firearm. FIGS. 7A-7D show data plots depicting exemplary results of the exemplary before and after GSR detection analysis obtained from the four different subjects, respectively, under the following exemplary conditions: C1: 1st Control; C2: $2^{nd}$ Control; and F: Firing (e.g., Fiocchi 40S&W in FIGS. 7A and 7B, and PMC® Bronze 45 in FIGS. 7C and 7D).

For example, the C1: 1st Control voltammetry waveform (black) displayed a small signal at a potential of −40 mV vs. Ag/AgCl, which may be attributed to trace levels of Cu. For example, the C2: $2^{nd}$ Control voltammetry waveform (red) showed two signals at −400 mV and 0 mV vs. Ag/AgCl, which may be attributed mainly to Pb and Cu/Sb contributions, respectively. For example, the Pb signal was not present prior to exposure to GSR but substantially increased thereafter. Also for example, the levels of Cu and Sb also became elevated when compared to C1. The increase in these signals was consistent over the four different subjects, e.g., despite no steps taken to moderate the length of time and proximity to the discharge of firearms. This exemplary signature demonstrates that GSR can travel not only to the shooter, but also to observers in their vicinity.

Figure 7A:
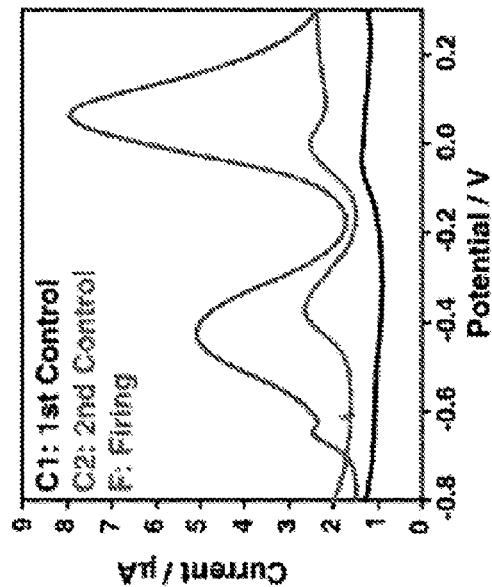
FIGS. 7A-7D show data plots depicting exemplary results produced by the exemplary 'swipe-and-scan' technique for before and after GSR exposure analysis.
Figure 7B:
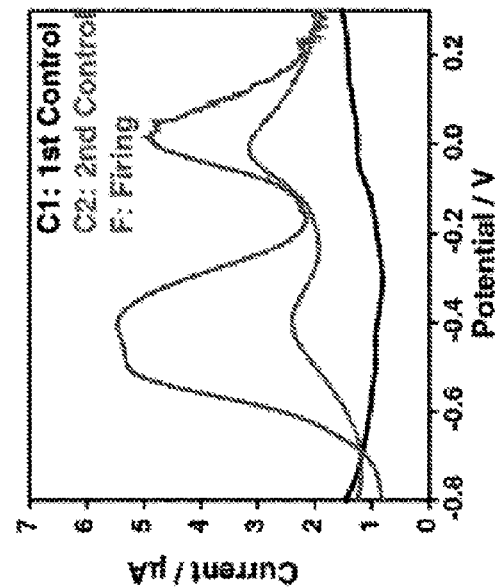
Figure 7C:
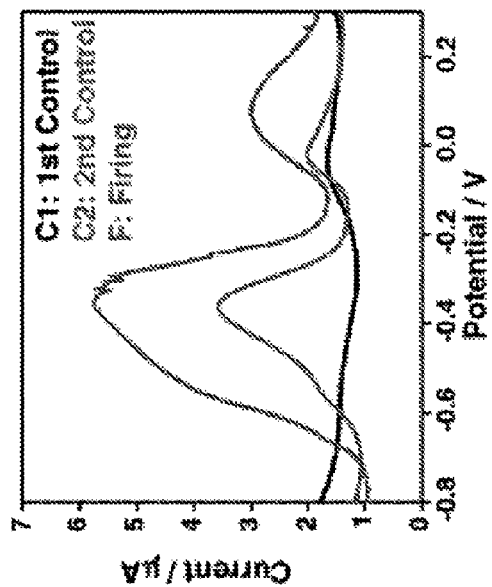
Figure 7D:
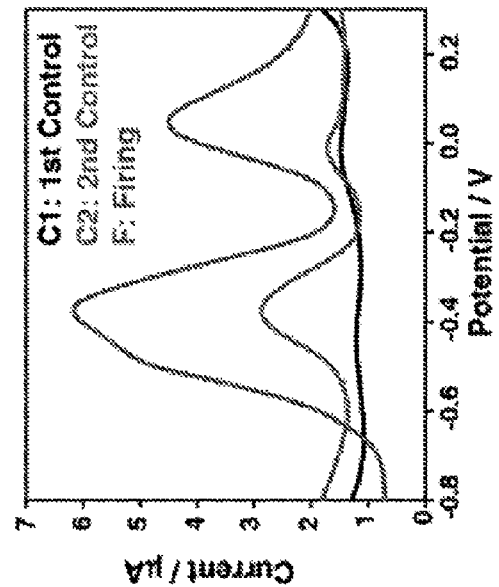

For example, the signature from a strip taken post-discharge of a firearm, F: Firing (green) shows a significant increase in the electrochemical signals of Pb at −400 mV vs. Ag/AgCl, and the peak corresponding to Cu/Sb at 0 mV. For example, another signal was observed at −600 mV, which may be attributed to the stripping of a Pb/Cu or Pb/Sb amalgam, as it increases with higher Sb/Cu signals. Therefore, it is shown that the level of GSR on the hands of a shooter greatly exceeds that on the hands of an observer. However, varying levels of GSR may be present on the hands of a shooter for discharge of fewer rounds. The data plots of FIGS. 7A-7B show a consistent trend in current magnitudes for the four exemplary subjects: C1<C2<F. It is noted, for example, that the presence of fatty acids from the hands of the subjects did not impede the exemplary analysis of the metallic components in GSR using the disclosed techniques.

Figures 8A, 8B, 8C, 8D:
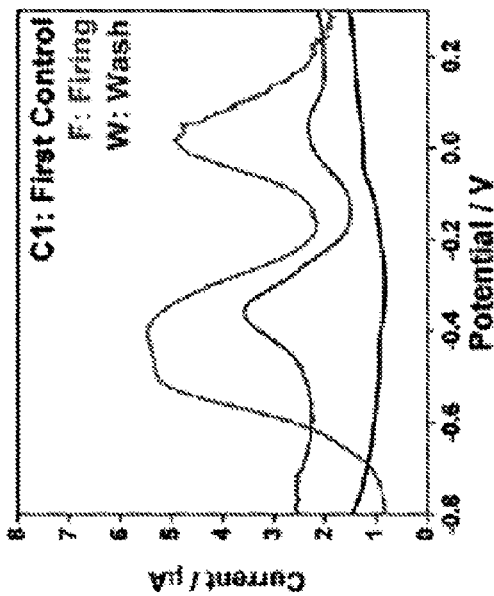
FIGS. 8A-8D show data plots depicting exemplary results produced by the exemplary 'swipe-and-scan' technique for hand-washing and loading effects on GSR exposure analysis.

The exemplary implementations included the investigation of the effect of hand washing and loading by the subject on the exemplary AbrSV 'swipe-and-scan' technique for the detection of GSR. FIGS. 8A and 8B show data plots depicting exemplary voltammetric signatures of samples from subjects who have discharged a firearm shown in green: F: Firing (e.g., Fiocchi 40S&W in FIG. 8A and PMC® Bronze 45 in FIG. 8B), samples taken post-hand-washing in blue (W: Wash) from the subjects who discharged the firearm, and samples representing C1:$1^{st}$ Control (black).

For example, the exemplary hand wash condition (W: Wash) shows a decrease in the Pb and Cu signals at −400 mV and 0 mV vs. Ag/AgCl, respectively. However, the magnitude of the current for both these signals is still greater than those observed prior to the subjects' contact with a firearm, C1: $1^{st}$ Control. This exemplary data substantiates that significant effort must be made to remove traces of GSR from the hands after exposure to GSR or the discharge of the firearm.

The effect of the exemplary AbrSV 'swipe and scan' technique was also examined on the hands of subjects who loaded the firearm, compared with voltammetry after discharge. FIGS. 8A and 8B show data plots depicting exemplary voltammetric signatures of samples from subjects who have discharged a firearm shown in green, F: Firing (e.g., Fiocchi 40S&W in FIG. 8C and PMC® Bronze 45 in FIG. 8D), sample results for C1:$1^{st}$ Control (black), and AbrSV samples taken from the hands of the corresponding subject subsequent to loading the firearm, labeled L: Loading (magenta). For example, a significant increase in the level of Cu for the L: Loading scans was observed, e.g., as compared to the corresponding discharge of the firearm. For example, this may be due to increased exposure to Cu from the brass bullet casing. Also for example, the levels of Pb were also comparable with those detected upon discharge of the firearm, whereby the overall signatures of GSR are similar, e.g., suggesting that high levels of GSR remain on the firearm from previous discharge.

III. Exemplary Implementations for Simultaneous Electrochemical Measurement of Metal and Organic Propellant Constituents of Gunshot Residue Exemplary implementations of the disclosed chemometric systems, devices, and techniques are described that are capable of simultaneous electrochemical measurement of heavy-metal and organic propellants relevant to GSR. For example, in these exemplary implementations, techniques are described (e.g., using cyclic voltammetry (CV) and cyclic square-wave stripping voltammetry (C-SWV)) to detect in a single run common propellants, e.g., such as nitroglycerin (NG) and dinitrotoluene (DNT), along with the antimony (Sb), lead (Pb), zinc (Zn) and barium (Ba) heavy metal constituents of GSR. Also, for example, the voltammetric detection can include the stabilizer diphenylamine (DPA), along with inorganic constituents. As shown in the exemplary results of the exemplary implementations, the resulting electrochemical signatures combine—in a single voltammogram—the response for the various metals and organic species, e.g., based on the reduction and oxidation peaks of the constituents. Cyclic square-wave voltammetry at the glassy carbon electrode (GCE), involving an intermittent accumulation at the reversal potential of −0.95 V (e.g., for Sb, Pb, DNT and NG) and −1.3 V (e.g., for Sb, Pb, Zn and DPA) was shown to be particularly useful to offer distinct electrochemical signatures for these constituents of GSR mixtures, e.g., as compared to analogous cyclic voltammetric measurements. Simultaneous voltammetric measurements of barium (at thin-film Hg GCE) and DNT (at bare GCE) were also demonstrated in connection to intermittent accumulation at the reversal potential of −2.4V. The disclosed systems and methods can provide single-run information of rich inorganic/organic electrochemical fingerprints that can be implemented in 'on-the-spot' field identification of individuals firing a weapon, e.g., as desired for diverse forensic investigations at a crime scene or battlefield.

Among the metallic constituents of gunshot residues, antimony (Sb), lead (Pb) and barium (Ba) are nearly universally found in relatively high levels on the handler of a firearm subsequent to a discharge. Such inorganic gunshot residues are commonly analyzed using large metal analyzers based on graphite-furnace atomic absorption spectroscopy or inductively-coupled plasma-atomic emission spectrometry. However, these existing techniques are costly and bulky with respect to equipment, and require specialized personnel. Aside from this factor, the detection of these species alone can be inconclusive in criminal investigations if the amounts of these species are below a certain threshold level since minimal amounts of these are not unique to GSR. For example, antimony is found in several alloys and oxides for fire retardants, lead is found in plumbing materials, solder and glass, and barium is found in paint and auto grease. In fact, workers in auto mechanic, electricity, and construction industries are found to have higher levels of these metals on their hands. The disclosed systems, devices, and techniques are capable of analyzing these heavy metals with that of additional constituents, e.g., such as organic ones, and thus be used to enhance the reliability of GSR forensic investigations.

For example, organic GSR compounds, such as nitroglycerin (NG) and dinitrotoluene (DNT), are found in primer mixtures and smokeless gunpowder, but can also originate from every part of the ammunition used. Other organic constituents found in GSR include stabilizers such as diphenylamine (DPA) and ethyl centralite (EC). For example, these are added to smokeless gunpowders to prevent the decomposition of species such as NG. In a study of 33 common smokeless gunpowders, DPA, NG and DNT were among the major components detected. NG can be used as a target analyte for GSR determination in double and triple-base powders, and since there are no known environmental sources of NG, its presence is indicative of discharge of a firearm or presence of explosives. For example, when a firearm is used, some unburned gunpowder is invariably blown down the barrel since efficiency of the combustion of the powder is less than 100%. While organic compounds can be analyzed using chromatographic or electrophoretic separation techniques, there are no existing techniques to provide the simultaneous measurements of organic and inorganic constituents of GSR.

III.1. Exemplary Materials and Methods

Exemplary chemicals and materials used in the described exemplary implementations included acetate (e.g., 0.1M, pH 4.5), which was prepared from acetic acid and sodium acetate; lithium perchlorate and mercury(II) nitrate monohydrate; and 0.1 M solutions of $LiClO_4$ and $Hg(NO_3)_2$ that were prepared by dissolving the appropriate amounts of the materials in deionized water. The pH of the $LiClO_4$ and $Hg(NO_3)_2$ solutions were 6.8 and 2.9, respectively. The exemplary chemicals and materials also included acetonitrile and nitroglycerin stock solution (e.g., 1000 μg/mL in acetonitrile). Dinitrotoluene standard solution (e.g., 1000 μg/mL) was prepared in acetonitrile. Diphenylamine was obtained, and a standard solution was prepared by dissolving the solid in acetonitrile. Standard solutions of lead, zinc, and antimony were prepared from atomic absorption standard solutions (e.g., 1000 µg/mL). A standard solution of barium was prepared from an atomic absorption standard solution (e.g., 1000 µg/mL). Deionized water (e.g., 18 Me-cm) was used to prepare all solutions. Exemplary electrochemical measurements for Pb, Sb, Zn, DPA and explosives were carried out using a 0.1 M acetate buffer solution (e.g., pH 4.5), whereas barium/DNT analysis was conducted in 0.1 M $LiClO_4$.

The exemplary electrochemical measurements for metals, DPA, and explosives were performed using a portable electrochemical analyzer EmStat (e.g., PalmSens, The Netherlands), connected to a laptop PC, and data were collected using the PS Trace 1.2 software. Barium analysis was conducted with a CHI 1230A electrochemical analyzer (e.g., CH Instruments, Inc., Austin, Tex.). The exemplary electrochemical measurements were performed at room temperature (e.g., ~23° C.) using a three-electrode electrochemical cell containing a glassy carbon disk (e.g., 2 mm) working electrode, a platinum wire auxiliary electrode, and an Ag/AgCl reference electrode. Prior to its use, for example, the glassy carbon electrode was thoroughly polished with 0.05 µm alumina slurry on a felt pad and cleaned by ultrasonication for 30 s.

In the exemplary implementations, the electrochemical organic/inorganic signatures for Sb, Pb, DNT and NG were obtained by cyclic voltammetry and cyclic square wave voltammetry. Cyclic voltammograms were measured for the first two cycles under the following parameters, for example, $E_{init/final}$ 1.15V; $E_2$, −0.95V; scan rate, 10 mV s$^{-1}$, and $E_{step}$ of 4 mV (staircase voltammetry). The second cycle was recorded and used for subsequent analysis.

For example, the square wave voltammograms for Sb, Pb, DNT and NG were recorded by first scanning reductively from initial potential 1.15 V to −0.95 V, then holding the potential at −0.95 V for 120 s without stirring, and finally sweeping back anodically to the initial 1.15 V potential. The square-wave voltammetric parameters were as follows, for example, amplitude, 25 mV; $E_{step}$, 4 mV; frequency, 8 Hz; equilibration time ($t_{eq}$), 5 s; SWV (Reduction): $E_{initial}$, 1.15 V; $E_{final}$, −0.95 V; SWV (oxidation): $E_{init}$, −0.95 V; $E_{final}$, 1.15 V; and $t_{accum}$ of 120 s. Square wave voltammograms for mixtures of Sb, Pb, Zn, and DPA were recorded in a similar fashion, but using different parameters specified herein.

For the analysis of the barium/DNT mixture, for example, a 2 mL sample solution in 0.1 M $LiClO_4$ was added to an electrochemical cell. Square-wave voltammetric detection of DNT was conducted by sweeping the potential from 0.00 V to −2.40 V at a bare glassy carbon working electrode. After the SWV analysis of DNT was completed, 100 µL of 0.1 M $Hg(NO_3)_2$ solution was added immediately to the sample solution. An accumulation potential ($E_{init,accum}$) of −2.40 V was applied for 180 s in the $LiClO_4$ electrolyte containing 5 mM $Hg^{2+}$ species under stirring for the codeposition of Hg and Ba at the glassy carbon electrode. Anodic square-wave stripping analysis of barium was then carried out by sweeping the potential from −2.40 V to +0.10 V.

III.2. Exemplary Results of the Exemplary Implementations for Simultaneous Electrochemical Measurement of Metal and Organic Propellant Constituents of GSR In the exemplary implementations, a cyclic square-wave voltammetric (C-SWV) operation is coupled with an intermittent accumulation (at the reversal potential) to provide a particularly sensitive, distinct, and rapid simultaneous response for multiple organic and inorganic constituents of GSR, e.g., reflecting the effective background compensation and speed of SWV, as well as the preconcentration process (compared to common cyclic voltammetric signatures).

Figure 9:
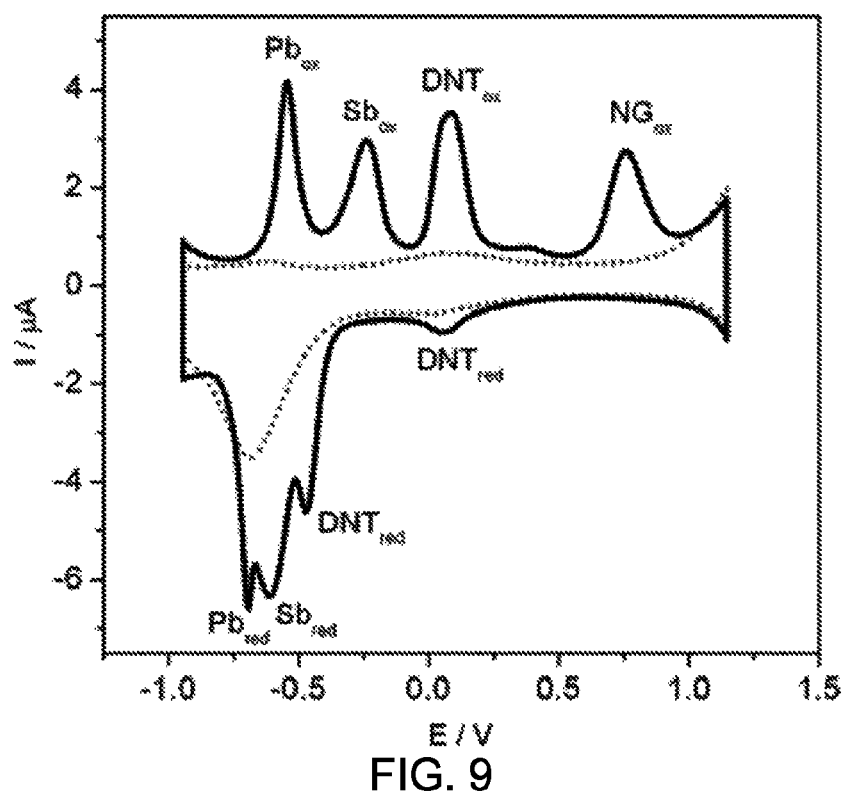
FIG. 9 shows an exemplary cyclic square-wave voltammogram for an exemplary mixture of GSR constituents at a bare glassy-carbon electrode (GCE).

FIG. 9 shows a cyclic square-wave voltammogram of an exemplary bare glassy-carbon electrode (GCE) for a mixture of four GSR constituents, e.g., including two heavy metal ion $Sb^{3+}$ and $Pb^{2+}$ and the two propellants NG and DNT. For example, the exemplary mixture of trace metals and explosives constituents of GSR included 3 ppm Pb, 10 ppm Sb, 50 ppm NG, 10 ppm DNT. For example, the square wave parameters included $E_{step}$, 4 mV; amplitude, 25 mV; frequency, 8 Hz; $t_{eq}$, 5 s; (Reduction) $E_{start}$, 1.15V; $E_{stop}$, −0.95V; (Oxidation) $E_{start,accum}$, −0.95V; $E_{stop}$, 1.15V; $t_{accum}$, 120 s. Electrolyte, acetate buffer (pH=4.5).

In the cyclic square-wave voltammogram of FIG. 9, for example, a SWV was first swept from 1.15 V to −0.95 V reducing the explosives and metal ions. For example, the potential was held at −0.95 V for 120 s and a SWV was swept back to 1.15 V, oxidizing and stripping the reduced products. This exemplary cyclic operation resulted in well-defined voltammogram with distinct peaks of the metal/metal ion and propellant species. The forward scan shows four well defined cathodic peaks, e.g., corresponding to the reduction of DNT ($E_{p,\ red}$=0.058V and −0.471V), $Sb^{3+}$ ($E_{p,\ red}$=−0.623V) and $Pb^{2+}$ ($E_{p,\ red}$=−0.698). The reduction of DNT proceeds via a stepwise reduction of each nitro group to a hydroxylamine group, and further reduction of the hydroxylamine to an amine group. The reduction of NG was not observed in this scan as it occurs too near solvent breakdown, but is known to proceed via a 2-electron reduction of each nitro group to form an alcohol group and a nitrite ion. The forward scan also shows Sb and Pb signals at more negative potentials where they are reduced at the electrode surface to metallic $Pb^0$ and $Sb^0$. On the reverse scan, four anodic peaks were observed. The signals observed at −0.546 and −0.242 V (vs. Ag/AgCl) are stripping peaks for Pb and Sb metals, respectively. The signals observed at potentials 0.081 V and 0.766 V are attributed to the oxidation of the reduction products of DNT and NG, respectively.

The exemplary cyclic square-wave voltammogram shown in FIG. 9 clearly illustrates the advantages of examining simultaneously both the cathodic as well as the anodic signals, of both the metal and explosives species, whereby the anodic signals display a more defined signal for Pb, Sb and DNT, as well as providing the only signal in the SWV for NG. As shown in the figure, for example, the anodic signals, while not necessarily of greater current magnitude than the cathodic ones, are certainly more defined and resolved.

Table 4 shows a summary of peak potentials, E, and peak currents, I, from the exemplary cyclic square-wave voltammogram of FIG. 9.

TABLE 4

| GSR/ Explosive | E(O)/ V | I(O)/ µA | E(R)/ V | I(R)/ µA | I (R)/I (O) | ΔE (50% I)/ V |
|---|---|---|---|---|---|---|
| Pb | −0.55 | 3.42 | −0.70 | −5.34 | −1.56 | 0.082 |
| Sb | −0.24 | 2.01 | −0.62 | −4.98 | −2.48 | 0.120 |
| NG | 0.77 | 2.89 | | | | 0.131 |
| DNT | 0.08 | 1.77 | 0.06 −0.47 | −0.48 −3.45 | −0.27 | 0.146 |

Also, for example, additional information can be extracted from the shape and width of these 8 peaks and further contribute to the overall information content. Table 4 also shows the peak width at 50% peak current, which can be utilized to characterize the signals observed. Such a distinct voltammetric pattern thus provides a unique fingerprint of the heavy-metal/propellant mixture. The coupling of the charging-current compensation with the accumulation of the metals and explosive reduction products leads to a sensitive and distinct response for these ppm levels of the four exemplary GSR constituents.

Figure 10:
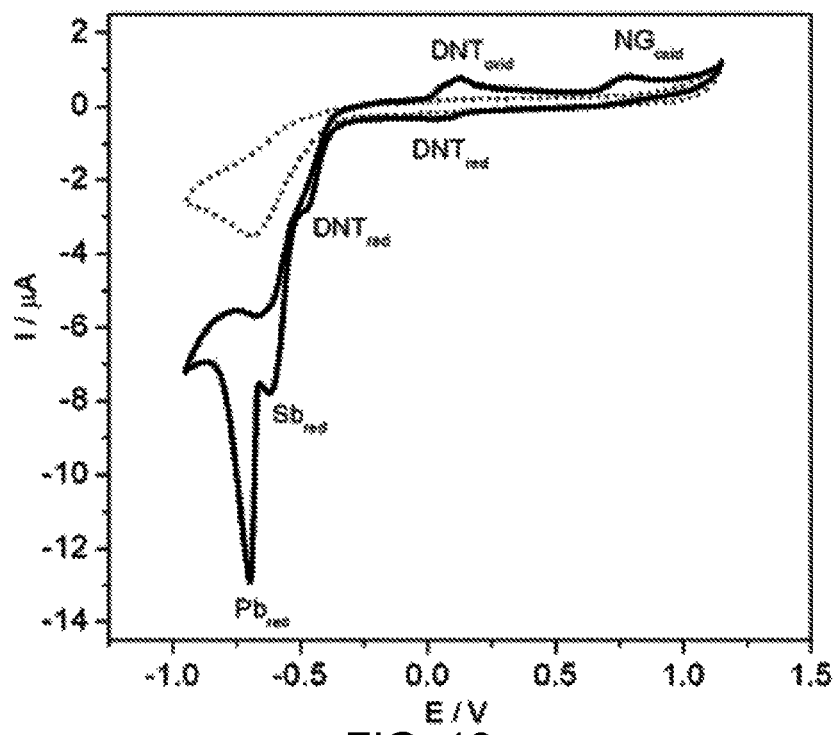
FIG. 10 shows an exemplary cyclic voltammogram for an exemplary mixture of GSR constituents at a bare GCE.

Cyclic voltammetry (CV), which is widely used for obtaining qualitative information in electroanalytical chemistry, can also lead to a distinct voltammetric pattern for mixtures of the metal ion/propellant constituents of GSR. FIG. 10 shows a cyclic voltammogram conducted at an exemplary bare GCE for such an inorganic/organic mixture, e.g., containing 3 ppm $Pb^{2+}$, 10 ppm $Sb^{3+}$, 50 ppm NG, and 10 ppm DNT in an acetate buffer medium (e.g., pH=4.5). In this example, the voltammogram was swept from potential 1.15 V to −0.95 V, and reversed back to 1.15 V (e.g., $E_{1, stop}$, 1.15 V; $E_2$, −0.95 V; scan rate, 10 mV/s; $E_{step}$, 4 mV).

As shown in FIG. 10, the cyclic voltammogram contains six signals, e.g., including four cathodic signals corresponding to the reduction of DNT (0.053 V and −0.477 V), $Sb^{3+}$ (−0.598 V), and $Pb^{2+}$ (−0.686 V), and two oxidation peaks of the DNT (0.124 V) and NG (0.778 V) reduction products. A similar voltammogram recorded using an intermittent 120 s accumulation period (at the reversal potential) yielded a very similar response with the exception of a small Pb stripping signal at −0.50 V. For example, similar to the cyclic square-wave voltammogram of FIG. 9, the cathodic signals in the cyclic voltammogram of FIG. 10 can be attributed to the reduction of DNT, $Sb^{3+}$ and $Pb^{2+}$, while the oxidation signals can be attributed to the oxidation of the reduced DNT and NG species. However, for example, unlike the cyclic square-wave voltammogram response of FIG. 9, anodic stripping metal peaks were not observed for the cyclic voltammogram of FIG. 10.

Table 5 shows a summary of the peak potentials from the exemplary cyclic voltammogram of FIG. 10.

TABLE 5

| Analyte | E(O)/V | I(O)/μA | E(R)/V | I(R)/μA |
|---|---|---|---|---|
| Pb | | | −0.69 | −5.50 |
| Sb | | | −0.60 | −0.48 |
| NO | 0.78 | 0.24 | | |
| DNT | 0.12 | 0.42 | 0.05 | −0.08 |
| | | | −0.48 | −0.340 |

It is noted, for example, while rich in their information content, such cyclic voltammetric signatures do not offer equivalent resolution to the cyclic square-wave voltammetric patterns in terms of overall signal-to-background characteristics and sharpness of the individual peaks. For example, while the cyclic square-wave voltammogram of FIG. 9 shows clear and sharp stripping signals for the two target metals, no such metal signals are visible in FIG. 10. The exemplary signals for DNT and NG are also more distinguishable in FIG. 9, as compared to the cyclic voltammogram of FIG. 10, e.g., with current outputs of 2.89 μA and 1.77 μA respectively, compared to 0.24 μA and 0.42 μA in the CV.

Figure 11:
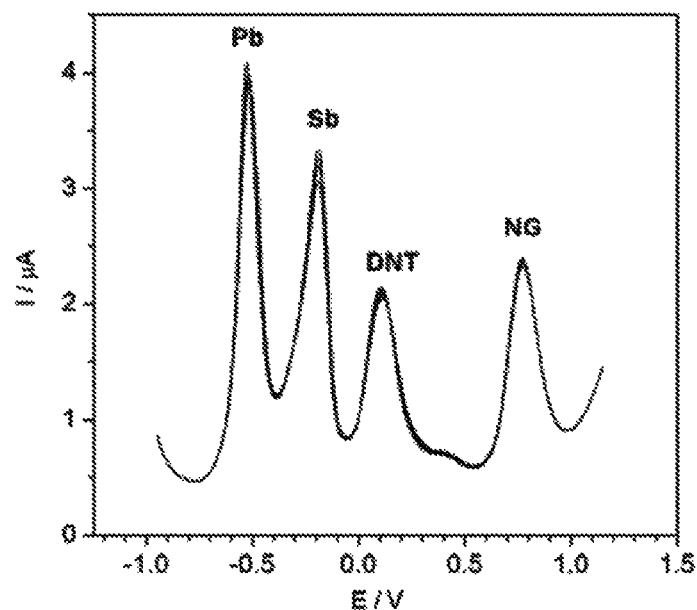
FIG. 11 shows a data plot of six exemplary repetitive anodic square-wave voltammograms for an exemplary mixture of GSR components at a bare GCE.

Square-wave voltammograms, following accumulation at −0.95V, offer particularly distinct sharp oxidation peaks for the inorganic/organic GSR mixture. Such SW voltammograms are highly reproducible, e.g., which is important in forensic investigations. FIG. 11 shows a data plot of six exemplary repetitive anodic square-wave voltammograms for an exemplary mixture containing $Pb^{2+}$ (e.g., 3 ppm Pb), $Sb^{3+}$ (e.g., 10 ppm Sb), DNT (e.g., 10 ppm DNT), and NG (e.g., 50 ppm NG), following 2 min accumulation at −0.95 V and potential sweep to 1.15 V at a bare GCE. As shown in the data plot of FIG. 11, four well defined highly reproducible peaks are present, e.g., corresponding to the stripping of Pb and Sb metals (−0.5 V and −0.2 V, respectively) and to the oxidation of the DNT and NG reduction products (0.1 V and 0.76 V, respectively). There is little variation in the peak heights of each signal, reflecting the removal of the individual constituents from the electrode surface after each run. For example, no polishing steps were implemented between any of the scans indicating, not only the removal of constituents from the electrode surface, but also an absence of surface poisoning by the organic species. The good precision and absence of memory effects is reflected by the low relative standard deviations of 2.75% for Pb, 3.88% for Sb, 3.29% for DNT and 1.22% for NG. For example, the disclosed technology is able to implement with such high precision, obtained without intermittent polishing, which is important in practical forensic applications.

Figure 12:
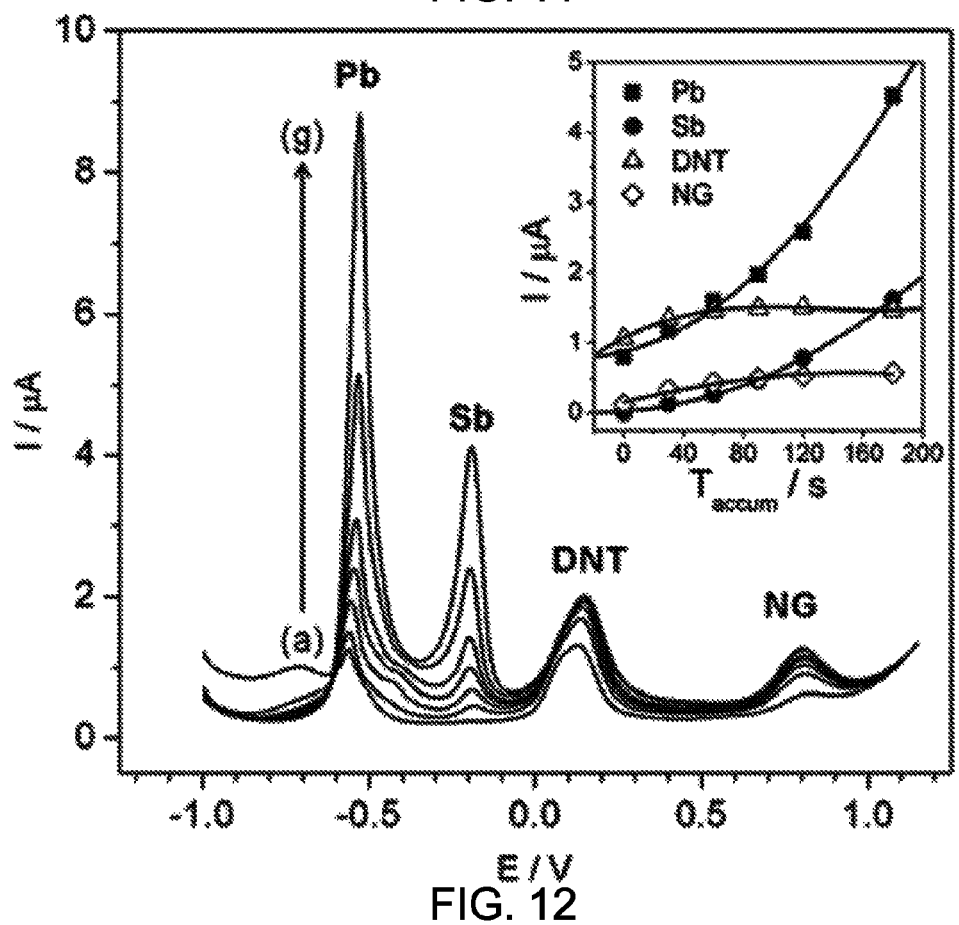
FIG. 12 shows a data plot of exemplary anodic square-wave voltammograms depicting the effect of accumulation time on the anodic signals of the exemplary mixture of heavy-metal and explosives constituents of GSR.

The exemplary implementations also included an examination of the exemplary GSR detection system in terms of accumulation time. For example, a range of accumulation times was applied prior to anodic stripping at a bare GCE. FIG. 12 shows a data plot of exemplary anodic square-wave voltammograms depicting the effect of accumulation time on the anodic signals of the exemplary mixture of heavy-metal and explosives constituents of GSR, e.g., 5 ppm Pb, 10 ppm Sb, 10 ppm, DNT, and 10 ppm NG. For example, a potential of −1.0 V was held for different accumulation times (e.g., 0, 30, 60, 90, 120, 150 and 180 s, corresponding to waveforms (a)-(g), respectively), after which a square-wave voltammogram was swept anodically to potential 1.15 V. For example, the voltammogram shows anodic signals for Pb, Sb, DNT and NG at −0.55 V, −0.24 V, 0.13 V and 0.77 V respectively. As shown in FIG. 12, the metal signals increase with increasing accumulation time, for example, the Pb response increases from current output 1.18 μA to 8.73 μA, and the Sb signal increases from 0.25 μA to 4.08 μA upon increasing the deposition time 0 to 180 s. As shown in FIG. 12, the anodic signals for the explosive species increase with increasing accumulation time initially, for example, from 1.3 μA to 1.8 μA for DNT, and 0.6 μA to 1.3 μA for NG. It is noted, for example, that these explosive signals level off for accumulation times in excess of 120 s. This dependence is displayed in the corresponding current-time plots for the four analytes (inset plot of FIG. 12). While a higher accumulation time can result in greater signal output for the metal stripping signals, it would be undesirable to maintain an accumulation resulting in the saturation of the explosive species signal. Therefore, for example, an accumulation time of 120 s was chosen in these exemplary implementations based on a good signal output for the metal stripping, without saturation of the explosive species.

Figure 13:
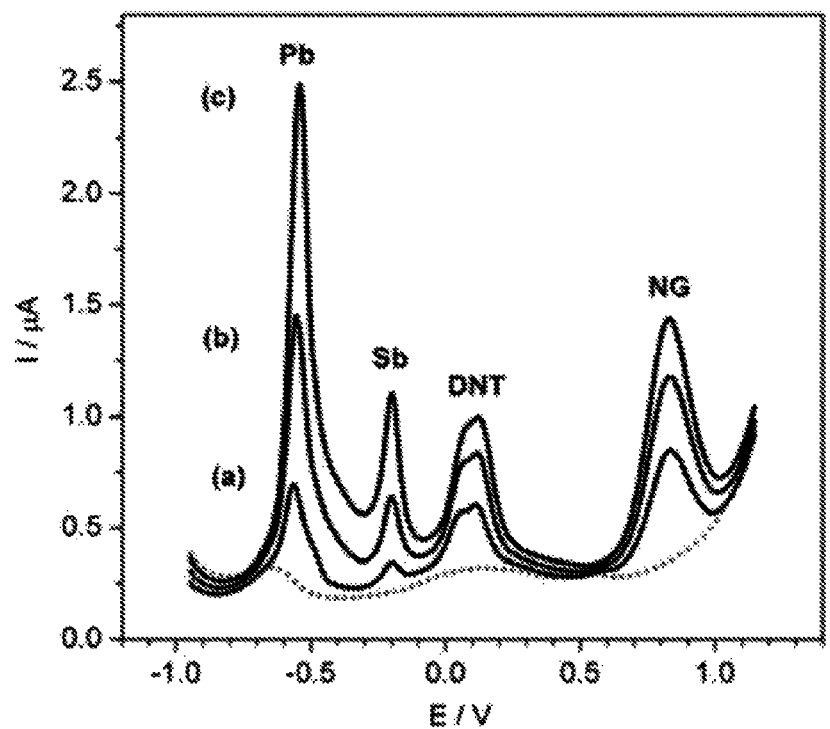
FIG. 13 shows a data plot of exemplary anodic square-wave voltammograms for exemplary mixtures containing increasing concentrations of metal and propellants.

The exemplary implementations included examination of the effect of concentration of the different metal ions and organic propellants upon the resulting voltammetric signatures. FIG. 13 shows a data plot of exemplary anodic square-wave voltammograms for exemplary mixtures containing increasing concentrations of metal and propellants. For example the concentration of metal ion and explosive in the mixtures corresponding to the waveforms (a)-(c) shown in FIG. 13 are: Pb (1, 2, 3 ppm); Sb (2, 4, 6 ppm); NG (5, 10, 15 ppm); DNT (1, 2, 3 ppm). A background voltammogram of acetate buffer (e.g., pH 4.5) is shown as the red dotted line. For example, SWV was carried out for each mixture concentration over the potential range of −0.95 V to 1.15 V, e.g., following a 120 s accumulation at the initial potential. The data plot of FIG. 13 shows that the analytical signals of the four constituents increase with increasing concentration in each case. For example, such quantitative data do not affect the qualitative information inherent to these voltammetric signatures, particularly as the peak potentials and shapes are independent of the concentration.

The challenging electrochemical detection of barium (Ba) was also examined in these exemplary implementations. For example, the presence of Ba is characteristic in the components of GSR. For example, it can also be a more significant target analyte than Pb since it does commonly present in as many products or environmental sources. The detection of Ba can present a larger challenge compared with the other two metals. For example, detection of Ba may require the presence of mercury either as an electrode surface or in an amalgam to achieve electrochemical detection. In these exemplary implementations of the disclosed technology, the simultaneous detection of $Ba^{2+}$ and DNT was examined. The ability to detect these two species together, as well as the ability to detect other metals and explosives, enhances the capabilities of the disclosed GSR electrochemical detection/signature approach.

Figure 14:
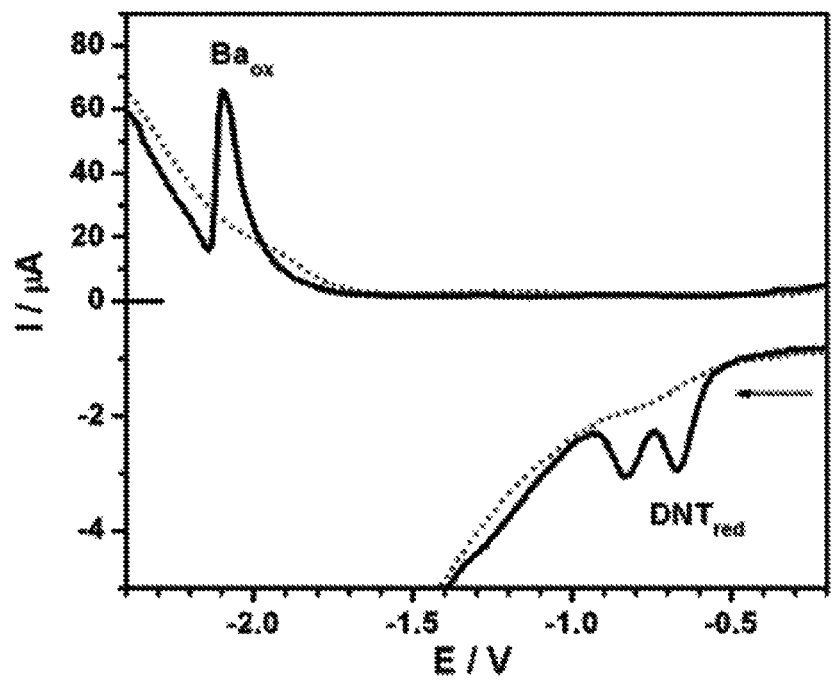
FIG. 14 shows a data plot of a cyclic square wave voltammogram for an exemplary mixture of barium and DNT at a thin-film Hg GCE and bare GCE, respectively.

FIG. 14 shows a data plot of a cyclic square wave voltammogram for an exemplary mixture of 0.5 ppm barium and 5 ppm DNT at a thin-film Hg GCE and bare GCE, respectively. For example, the square wave parameters included $E_{step}$, 10 mV; amplitude, 25 mV; frequency, 15 Hz; $t_{eq}$, 5 s; (Reduction) $E_{start}$, 0.00V, $E_{stop}$, −2.40V; (Oxidation) $E_{start,accum}$, −2.40V; $E_{stop}$, 0.10V; $t_{accum}$, 180 s. For example, 0.1 M lithium perchlorate (e.g., pH=6.8) was used as the electrolyte. As shown in FIG. 14, the cathodic SWV sweep between 0.0 V to −2.4 V resulted in two reduction signals for DNT at potentials −0.68 V and −0.72 V (vs. Ag/AgCl), corresponding to the reduction of the nitro groups to hydroxylamine groups. On reaching potential −2.4 V, the potential was held for accumulation time of 180 s, after which an anodic SWV was swept from −2.4 V to 0.0 V. The exemplary reverse scan resulted in a defined stripping peak for Ba at potential −2.09 V (vs. Ag/AgCl). For example, these exemplary results further demonstrate an analytical advantage of cyclic-SWV in conjunction with a preconcentration step in order to identify several species commonly or universally present in GSR. The identification of these signals enhances the ability of the exemplary GSR detection system of the disclosed technology to generate distinct metal/propellant GSR signatures using the described electrochemical methods. For example, the disclosed technique can couple Ba/DNT detection with the ability to detect other GSR constituents simultaneously, e.g., such as the four constituents shown in FIGS. 9-13, e.g., at individually addressable electrodes.

Figure 15:
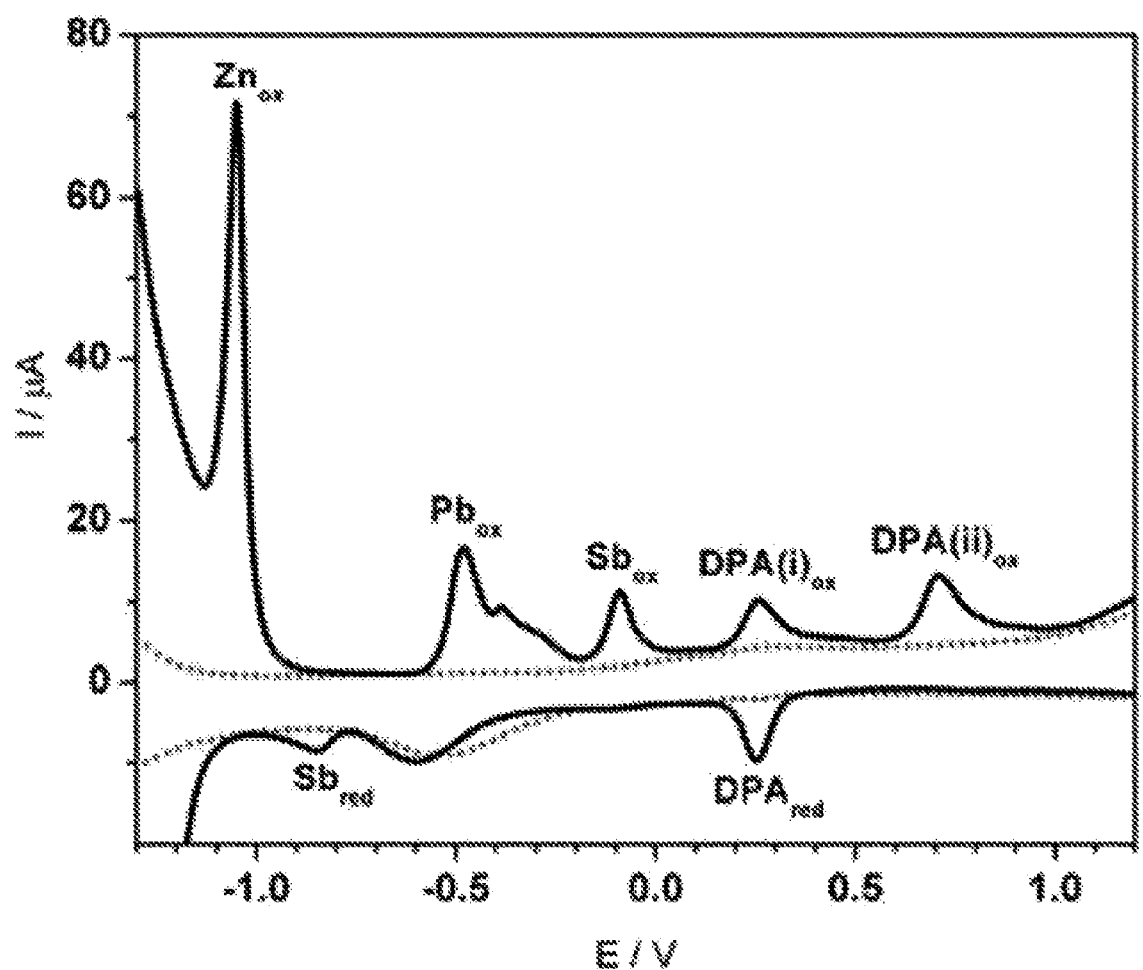
FIG. 15 shows a data plot of a cyclic square-wave voltammogram for an exemplary mixture of trace metals and explosives constituents of GSR.

The exemplary implementations included electrochemical detection of DPA, an organic stabilizer present in GSR, at a bare GCE. For example, DPA can be a constituent of smokeless gunpowder. FIG. 15 shows a data plot of a cyclic square-wave voltammogram for an exemplary mixture of trace metals and explosives constituents of GSR, e.g., including 2 ppm Zn, 2 ppm Pb, 20 ppm Sb, 200 ppm DPA. For example, the square wave parameters included: $E_{stop}$, 4 mV; amplitude, 25 mV; frequency, 25 Hz; $t_{accum}$, 120 s; (Reduction) $E_{start,accum}$ 1.2V; $E_{stop}$, −1.3V; (Oxidation) $E_{start,accum}$, −1.3V; $E_{stop}$, 1.2V; $t_{accum}$, 120 s. For example, acetate buffer (e.g., pH=4.5) was used as the electrolyte. As shown in FIG. 15, for example, the cathodic SWV sweep yielded a reduction signal for the oxidation products of DPA at potential 0.25 V (vs. Ag/AgCl), and a reduction signal for $Sb^{3+}$ at potential −0.85 V (vs. Ag/AgCl). For example, the anodic scan shows signals that may be attributed to metals Zn (−1.05 V), Pb (−0.5 V), Sb (−0.1 V), and two signals for the oxidation of the organic DPA and its reduction products (0.25 V and 0.75 V). For example, the exemplary reverse scan resulted in a well-defined electrochemical fingerprint for four species that are commonly found in GSR. For example, Zn has been found to be particularly prevalent in lead-free ammunition, and DPA comprises one of the five major volatile components frequently found in GSR. This exemplary single-run, information-rich metal/propellant fingerprint can provide 'on-the-spot' field identification of individuals firing a weapon.

The disclosed chemometric methods can be implemented to identify and analyze exposure levels of one or more chemical agents in a sample. For example, a sample can be collected (e.g., using a swipe and scan technique described herein or other sample collection techniques) and electrochemically analyzed. The disclosed chemometric methods include processing techniques that generate data to obtain an electrochemical spectral signature of the sample to identify the chemical agent(s). The disclosed chemometric methods include classification techniques to characterize an exposure level of a subject and/or surface from which the sample was collected to the identified chemical agent(s) present in the sample. For example, classification techniques include using predetermined data indicating different levels of exposure to the chemical agent or agents under different scenarios or conditions with the generated data associated with the chemical agent(s) to provide the determination or characterization of the level of exposure to the chemical agent(s). For example, the disclosed chemometric methods can provide the exposure level determination without performing subsequent processing, and can be implemented at the site of the collected sample, e.g., using the described systems and techniques of the disclosed technology.

Implementations of the subject matter and the functional operations described in this patent document can be implemented in various systems, digital electronic circuitry, or in computer software, firmware, or hardware, including the structures disclosed in this specification and their structural equivalents, or in combinations of one or more of them. Implementations of the subject matter described in this specification can be implemented as one or more computer program products, i.e., one or more modules of computer program instructions encoded on a tangible and non-transitory computer readable medium for execution by, or to control the operation of, data processing apparatus. The computer readable medium can be a machine-readable storage device, a machine-readable storage substrate, a memory device, a composition of matter effecting a machine-readable propagated signal, or a combination of one or more of them. The term "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, microcontrollers, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Computer readable media suitable for storing computer program instructions and data include all forms of nonvolatile memory, media and memory devices, including by way of example semiconductor memory devices, e.g., EPROM, EEPROM, and flash memory devices. The processor and the memory can be supplemented by, or incorporated in, special purpose logic circuitry.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described and other implementations, enhancements and variations can be made based on what is described and illustrated in this patent document.

What is claimed is:

1. A method to identify and analyze exposure levels of a chemical agent, comprising:
    collecting a sample from a surface containing a chemical agent to an electrode on a sensor to cause a contact between the chemical agent and the electrode;
    detecting an electrochemical signal of the chemical agent on the electrode to transduce chemical information associated with the chemical agent to an electrical signal;
    processing the electrical signal to generate data to obtain an electrochemical spectral signature from the data to identify the chemical agent;
    generating a series of coefficients of the electrochemical spectral signature to compress the data; and
    classifying the chemical information based on the series of coefficients among preselected data sets to determine a level of exposure to the chemical agent.

2. The method as in claim 1, wherein the collecting includes swiping the surface using the electrode surface of the sensor.

3. The method as in claim 2, wherein the sensor includes a printed three-electrode strip including a working electrode, a counter electrode, and a reference electrode, wherein the chemical agent is transferred to the working electrode.

4. The method as in claim 2, wherein the sensor includes a printed two-electrode strip including a working electrode and a reference electrode, wherein the chemical agent is transferred to the working electrode.

5. The method as in claim 1, wherein the detecting the electrochemical signal includes performing at least one of voltammetry, cyclic voltammetry, square wave voltammetry, differential pulse voltammetry, amperometry, chronoamperometry, potentiometry, chronopotentiometry, coulometry, chronocoulometry, conductometry, or impedometry.

6. The method as in claim 1, wherein the generating the series of coefficients of the electrochemical spectral signature includes using a discrete Wavelet transform (DWT) or a fast Fourier transform (FFT).

7. The method as in claim 6, further comprising using the DWT or the FFT to filter noise from the electrical signal.

8. The method as in claim 1, wherein the classifying includes performing pattern recognition using the preselected data sets and the series of coefficients to assign a group membership or ranking to the chemical information by maximizing inter-group variance between unique groups and minimizing intra-group variance.

9. The method as in claim 8, wherein the pattern recognition includes at least one of principal component analysis (PCA), analysis of variance (ANOVA), regression analysis, Fisher's linear discriminant (FLD), linear discriminant analysis (LDA), quadratic discriminant analysis (QDA), neural networks, perceptrons, support vector machines, Bayes classifiers, kernel estimation, decision trees, maximum entropy classifier, or K-means clustering.

10. The method as in claim 1, wherein the chemical agent includes gunshot residue (GSR).

11. The method as in claim 10, wherein the level of exposure to the GSR is classified into a plurality of groups including a No Contact group, a Secondary Contact group, and a Primary Contact group.

12. The method as in claim 11, wherein the Secondary Contact group includes subjects that have been present in an environment where a firearm was discharged (a) without a subject handling the firearm or (b) with the subject handling the firearm but not firing it.

13. The method as in claim 11, wherein the Primary Contact group includes subjects that have fired a firearm.

14. The method as in claim 13, wherein the Primary Contact group includes subjects that have fired the firearm and washed their hands subsequent to the firing of the firearm.

15. The method as in claim 1, wherein the chemical agent includes explosive residue (ER).

* * * * *